United States Patent
Adams et al.

(10) Patent No.: US 10,695,073 B2
(45) Date of Patent: Jun. 30, 2020

(54) CONTROL SYSTEM FOR RETROGRADE DRILL MEDICAL DEVICE

(71) Applicant: Arthrex, Inc., Naples, FL (US)

(72) Inventors: Ken Adams, Naples, FL (US); Daniela Garcia, Naples, FL (US); Philip S. O'Quinn, Naples, FL (US); James P. Bradley, Pittsburgh, PA (US); William R Beach, Glen Allen, VA (US)

(73) Assignee: Arthrex, Inc., Naples, FL (US)

( * ) Notice: Subject to any disclaimer, the term of this patent is extended or adjusted under 35 U.S.C. 154(b) by 135 days.

(21) Appl. No.: 15/683,434

(22) Filed: Aug. 22, 2017

(65) Prior Publication Data

US 2019/0059910 A1 Feb. 28, 2019

(51) Int. Cl.
*A61B 17/16* (2006.01)
*A61B 17/00* (2006.01)

(52) U.S. Cl.
CPC ........ *A61B 17/1626* (2013.01); *A61B 17/162* (2013.01); *A61B 17/1617* (2013.01); *A61B 17/1624* (2013.01); *A61B 17/1675* (2013.01); *A61B 2017/00367* (2013.01)

(58) Field of Classification Search
CPC .......................................... A61B 17/16–1697
See application file for complete search history.

(56) References Cited

U.S. PATENT DOCUMENTS

| | | | |
|---|---|---|---|
| 4,963,147 A | 10/1990 | Agee et al. | |
| 5,620,456 A | 4/1997 | Sauer et al. | |
| 5,913,867 A | 6/1999 | Dion | |
| 6,033,411 A | 3/2000 | Preissman | |
| 6,048,346 A | 4/2000 | Reiley et al. | |
| 6,053,907 A | 4/2000 | Zirps | |
| 6,358,251 B1 | 3/2002 | Mirza | |
| 6,464,711 B1 | 10/2002 | Emans et al. | |
| 6,478,801 B1 | 11/2002 | Ralph et al. | |
| 6,610,067 B2 | 8/2003 | Tallarida et al. | |
| 6,669,698 B1 | 12/2003 | Tromanhauser et al. | |
| 6,916,306 B1 | 7/2005 | Jenkins et al. | |

(Continued)

OTHER PUBLICATIONS

Joimax, "Shrill® Shaver Drill System: Multifunctional Drill and Resection System," joimax.com, accessed: Dec. 2016. http://www.joimax.com/us/_products/electronicdevices/shrill/.

(Continued)

*Primary Examiner* — Matthew J Lawson
(74) *Attorney, Agent, or Firm* — Akerman LLP; Michael K. Dixon

(57) ABSTRACT

A rotary, cutting medical device configured to be used during surgeries, such as ACL reconstruction, to drill holes and retrograde sockets is disclosed. The device may include a blade at a distal end that is movable between a first position aligned with a longitudinal axis of the device and a second position nonparallel to the longitudinal axis used to create retrograde sockets. The device may include a blade position control system connecting the blade to distal ends of both the outer tube and inner shaft and configured to control movement of the blade between first and second positions for drilling a hole and then creating a retrograde socket. The device may include a position retention system configured to retain the blade in the second position while allowing the inner shaft and blade to rotate to cut the socket.

17 Claims, 30 Drawing Sheets

(56) References Cited

U.S. PATENT DOCUMENTS

| | | |
|---|---|---|
| 6,923,813 B2 | 8/2005 | Phillips et al. |
| 6,976,987 B2 | 12/2005 | Flores |
| 7,029,479 B2 | 4/2006 | Tallarida et al. |
| 7,063,682 B1 | 6/2006 | Whayne et al. |
| 7,442,195 B1 | 10/2008 | Behrens |
| 7,569,057 B2 | 8/2009 | Liu et al. |
| 7,780,690 B2 | 8/2010 | Rehnke |
| 7,828,804 B2 | 11/2010 | Li et al. |
| 7,842,041 B2 | 11/2010 | Liu et al. |
| 8,021,366 B2 | 9/2011 | Phan |
| 8,057,477 B2 | 11/2011 | Desarzens et al. |
| 8,080,061 B2 | 12/2011 | Appenzeller et al. |
| 8,088,135 B2 | 1/2012 | Heisler |
| 8,343,158 B2 | 1/2013 | Birkbeck |
| 8,394,101 B2 | 3/2013 | Landes |
| 8,449,552 B2 | 5/2013 | Sanders |
| 8,465,491 B2 | 6/2013 | Yedlicka et al. |
| 8,480,673 B2 | 7/2013 | Yedlicka et al. |
| 8,480,682 B2 | 7/2013 | Howlett et al. |
| 8,535,311 B2 | 9/2013 | Schell |
| 8,591,514 B2 | 11/2013 | Sherman |
| 8,603,106 B2 | 12/2013 | Catanese et al. |
| 8,652,139 B2 | 2/2014 | Sterrett et al. |
| 8,758,378 B2 | 6/2014 | Mcfarlin et al. |
| 8,801,713 B2 | 8/2014 | Del et al. |
| 8,852,190 B2 | 10/2014 | Sherman |
| 8,852,201 B2 | 10/2014 | Schmieding et al. |
| 8,888,781 B2 | 11/2014 | Sterrett |
| 8,926,615 B2 | 1/2015 | Ek |
| 9,101,366 B2 | 8/2015 | Sterrett et al. |
| 9,101,371 B2 | 8/2015 | Assell et al. |
| 9,113,919 B2 | 8/2015 | Assell et al. |
| 9,119,639 B2 | 9/2015 | Kuntz |
| 9,149,283 B2 | 10/2015 | Assell et al. |
| 9,232,954 B2 | 1/2016 | Steiner et al. |
| 9,254,138 B2 | 2/2016 | Siegal et al. |
| 9,358,029 B2 | 6/2016 | Sikora et al. |
| 9,414,851 B2 | 8/2016 | Kecman et al. |
| 9,439,634 B2 | 9/2016 | Ries et al. |
| 9,439,693 B2 | 9/2016 | Childs et al. |
| 9,463,061 B2 | 10/2016 | Malackowski et al. |
| 9,480,485 B2 | 11/2016 | Aho et al. |
| 9,504,478 B2 | 11/2016 | Edwards et al. |
| 2005/0240193 A1 | 10/2005 | Layne et al. |
| 2008/0249481 A1* | 10/2008 | Crainich ............ A61B 17/1617 604/264 |
| 2014/0276844 A1* | 9/2014 | Bourque ............ A61B 17/1714 606/80 |
| 2015/0351777 A1* | 12/2015 | Lizardi ............ A61B 17/1622 606/80 |

OTHER PUBLICATIONS

Smith & Nephew. "PCL Reconstruction with the ACUFEX Director Drill Guide," smithnephew.com, Knee Series Technique Guide, Rev. A, Sep. 2008. https://www.smith-nephew.com/global/surgicaltechniques/sports%20med/acufex_director_pcl_10600437a_us.pdf.

Smith & Nephew. "Dyonics Platinum Series Blades," smith-nephew. com, Sterile Disposable Blades and Burrs, accessed: Dec. 2016. https://www.smithnephew.com/global/assets/pdf/temp/2012_sterile_disposable_blades_burrs_(copy1).pdf.

Corin. "LARS™ PCL: PCL Reconstruction and Reinforcement, Surgical Technique," coringroup.com, Rev 1, Jun. 2012. http://www.coringroup.com/document.php?o=637.

FH Orthopedics, "CoLS® Classic System," Crosslig®, fhorthopedics.com,Feb. 2009. http://www.fhorthopedics.com/publicmedia/original/118/75/en/200902_lt12et_col09_usv1.pdf.

Youtube, "CLANCY™ Anatomic Cruciate Guide Flexible Drill System with Asheesh Bedi, MD," youtube.com, Aug. 6, 2012. https://www.youtube.com/watch?v=swbJ5A88Lrg&feature=youtu.be.

World Intellectual Property Office, "International Search Report and Written Opinion," issued in PCT Application No. PCT/US2018/021994, dated May 23, 2018, documents of 11 pages.

* cited by examiner

CONTROL SYSTEM FOR RETROGRADE DRILL MEDICAL DEVICE

FIELD OF THE INVENTION

The invention relates to rotary cutting devices useful in arthroscopy, and more particularly, to flip retrograde cutting devices for drilling of sockets and tunnels for ACL reconstruction.

BACKGROUND

During arthroscopic surgery, a small incision is made in the skin covering the arthroscopic site or joint, and a cannula is inserted in the incision to provide a pathway for surgical devices to be placed in the joint and manipulated through arthroscopic visualization. Surgical devices inserted through cannulas must be long and thin, which creates limitations on devices for cutting tissue, as the diameter of the cannula ordinarily limits the width of the cutting implement.

Flip cutters have been used for retrograde drilling of sockets and tunnels for ACL reconstruction. The flip cutters have a blade, preferably a flip blade, that is configured to articulate between at least a first "straight" position, for example, substantially parallel to a longitudinal axis of the flip retrograde cutter, and at least a second "flip" position, for example, a non-parallel position relative to the longitudinal axis of the flip retrograde cutter. Using such a flip retrograde cutter, a recipient site socket can be created from the inside out using a retrograde technique with minimal incisions of distal cortices and reduced intraarticular bone fragmentation of tunnel rims. The blades of the flip cutters have been moved manually between the first and second positions to enable retrograde drilling of sockets and tunnels. A more efficient system for retaining in position and moving the blade of a flip cutter is needed.

SUMMARY OF THE INVENTION

A rotary, cutting medical device configured to be used during surgeries, such as ACL reconstruction, to drill holes and retrograde sockets is disclosed. The device may include a blade at a distal end that is movable between a first position aligned with a longitudinal axis of the device and a second position nonparallel to the longitudinal axis used to create retrograde sockets. The device may include a connection system connecting the inner shaft to the blade such that blade is movable between first and second positions for drilling a hole and then creating a retrograde socket. The device may include a blade position control system connecting the blade to distal ends of both the outer tube and inner shaft and configured to control movement of the blade between first and second positions for drilling a hole and then creating a retrograde socket. The device may include a position retention system configured to retain the blade in the second position for creating a retrograde socket. The position retention system retains the blade in the second position while allowing the outer tube, inner shaft and blade to rotate to cut the socket. The position retention system prevents the blade from inadvertently returning to the first position, which is aligned with the longitudinal axis, when the blade encounters heavy resistance drilling through bone.

In at least one embodiment, the rotary cutting device may be formed from an elongated body having a distal end, a proximal end, and a longitudinal axis. The elongated body may also include an outer tube and an inner shaft housed by the outer tube. The device may include a blade at the distal end of the body, wherein the blade is configured to rotate from a first position generally aligned with the longitudinal axis to a second, flip position which is nonparallel with the longitudinal axis. The device may include a blade position control system connecting the blade to distal ends of both the outer tube and inner shaft. The blade position control system may include a connection system connecting the inner shaft to the blade that allows the blade to move from the first position generally aligned with the longitudinal axis to the second, flip position which is nonparallel with the longitudinal axis and a cutting arris of the blade is exposed toward the proximal end of the elongated body for retrograde drilling of a hole when the blade is locked in the second, flip position. The blade position control system may include a cam in communication with a cam follower and in communication with the inner shaft for moving the blade into first and second positions. The blade position control system may also include a position retention system configured to retain the cam in a second position such that the inner shaft is retained in the second position, thereby retaining the cutting arris of the blade in position such that the cutting arris is exposed toward the proximal end of the elongated body while allowing the inner shaft and blade to rotate for retrograde drilling of a hole.

The position retention system may be configured such that the position retention system may include one or more pins extending from the cam. The position retention system may include one or more grooves on the inner shaft for receiving the pin extending from the cam such that the inner shaft is rotatable while the pin resides in the groove on the inner shaft, thereby preventing axial movement of the inner shaft. The position retention system may include one or more slots in the cam for receiving the pin to account for potential misalignment between the pin, cam and groove on the inner shaft.

The cam of the blade position control system may be formed from a first head member and a second head member separated by a tube receiving chamber configured to receive the inner shaft extending therethrough. The cam follower may include a first position retainer configured to retain the cam in a first position, which also retains the blade in a position generally aligned with the longitudinal axis. The cam follower may also include a second position retainer configured to retain the cam in a second position in which the cutting arris of the blade is positioned such that the cutting arris is exposed toward the proximal end of the elongated body for retrograde drilling of a hole while allowing the inner shaft and blade to rotate. The first position retainer may be formed from a nonlinear engaging surface with a concave detent configured to hold the cam in a first position, which also retains the blade in a position generally aligned with the longitudinal axis. The engaging surface of the cam follower between the first and second position retainers may be nonorthogonal relative to the longitudinal axis of the elongated body. The second position retainer may be formed from a flat surface generally orthogonal to the longitudinal axis of the elongated body. The second position retainer may be positioned closer to the distal end of the elongated body than the first position retainer.

The device may also include a housing configured to retain the cam in position whereby the housing includes an inner side surface that houses the cam to prevent the cam from being inadvertently displaced and to limit rotation of the cam about only one axis. The device may also include a biasing mechanism configured to bias the cam follower towards the cam to keep the cam follower in contact with the cam and configured to bias the inner shaft toward the distal end of the elongated body. The device may include a drive hub positioned at the proximal end and configured to place the inner shaft in mechanical communication with a handpiece to impart rotary motion to the inner shaft and blade, as controlled by controls on the handpiece.

In at least one embodiment, the connection system connecting the inner shaft to the blade may be formed from a pin and a slot that allow conversion of linear movement of the inner shaft into rotational movement of the blade to rotate the blade to the second, flip position. The blade rotates to the second, flip position upon linear movement of the inner shaft in relation to the outer tube the pin sliding in the slot to permit rotation of the blade. When the blade is in the second, flip position, the blade is articulated to a nonparallel position relative to the longitudinal axis of the elongated body. Also, when the blade is in the second, flip position, a cutting arris of the blade is exposed toward the proximal end of the elongated body for retrograde drilling of a hole.

An advantage of the device is that a user, such as, but not limited to, a surgeon, may use the handpiece to create retrograde sockets without the blade inadvertently popping out of position and requiring the blade to be repositioned before continuing to drill a retrograde socket.

Another advantage of the device is that position retention system prevents any lateral movement, thereby preventing the blade from inadvertently popping out of position, while enabling rotary motion to enable the blade to be rotated to cut bone.

Yet another advantage of the device is that the blade position control system moves the blade between a first positioned generally aligned with a longitudinal axis of the elongated body to a second flipped position in which the blade is nonparallel with the longitudinal axis and positioned to create retrograde sockets.

Another advantage of the device is that the blade control system may be controlled by a user, such as, but not limited to, a surgeon, via a single lever.

Still another advantage of the device is that the position retention system improves the safety of the device because the position retention system, outer hub and lever arm do not spin; rather, only the inner shaft spins, and in at least one embodiment, only the inner shaft and outer tube spin.

These and other embodiments are described in more detail below.

DETAILED DESCRIPTION OF THE FIGURES

Figure 1:
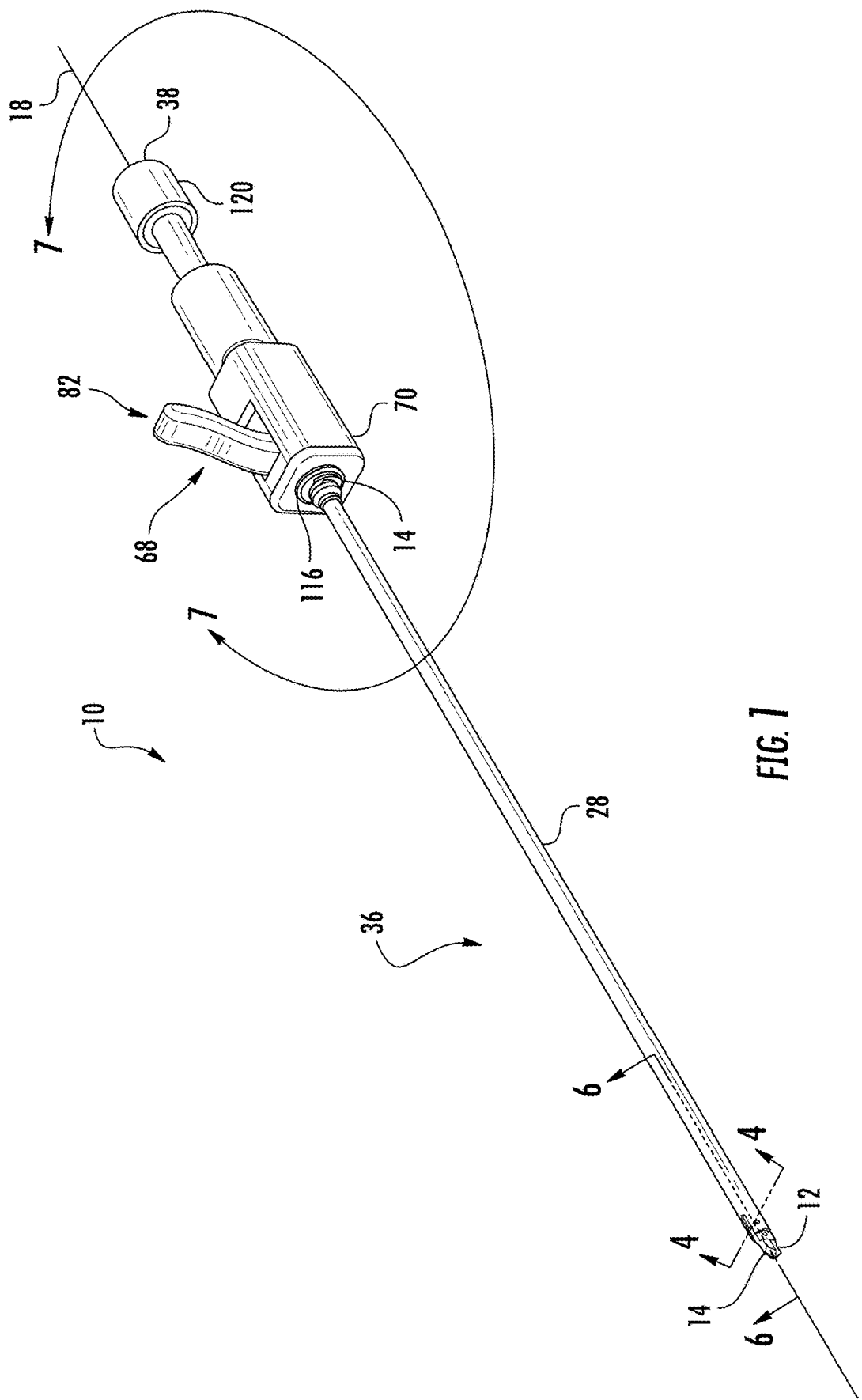
FIG. 1 is a perspective view of the rotary, cutting medical device.

As shown in FIGS. 1-36, a rotary, cutting medical device 10 configured to be used during surgeries, such as ACL reconstruction, to drill holes and retrograde sockets is disclosed. The device 10 may include a blade 12 at a distal end 14 that is movable between a first position 16 aligned with a longitudinal axis 18 of the device 10 and a second position 20 nonparallel to the longitudinal axis 18 used to create retrograde sockets 32 and tunnels. The device 10 may include a connection system 22 connecting an inner shaft 24 to the blade 12 such that blade 12 is movable between first and second positions 16, 20, as shown in FIGS. 15-27 for drilling a hole 24 and then creating a retrograde socket 32 or tunnel. The device 10 may include a blade position control system 26 connecting the blade 12 to distal ends 15, 17 of both the outer tube 28 and inner shaft 24 and configured to control movement of the blade 12 between first and second positions 16, 20 for drilling a hole 30 and then creating a retrograde socket 32 or tunnel. The device 10 may include a position retention system 34, as shown in FIGS. 7 and 9-13, configured to retain the blade 12 in the second position 20, as shown in FIGS. 16, 20 and 25-27, for creating a retrograde socket 32 or tunnel. The position retention system 34 retains the blade 12 in the second position 20 while allowing the inner shaft 24 and blade 12 to rotate to cut the socket. The position retention system 34 prevents the blade 12 from inadvertently returning to the first position 16, which is aligned with the longitudinal axis 18, when the blade 12 encounters heavy resistance drilling through bone.

In at least one embodiment, the rotary cutting device 10 may be formed from an elongated body 36 having a distal end 14, a proximal end 38, and a longitudinal axis 18. The elongated body 36 may also include the outer tube 28 and the inner shaft 24 housed by the outer tube 28. The inner and outer tubes 24, 28 may be formed from materials such as, but not limited to, 17-4 ph or 17-7 ph stainless steel. The inner shaft 24 may be sized to fit within the outer tube 28 while generally being aligned with the outer tube 28.

The device 10 may include a blade 12 at the distal end 14 of the body 36. The blade 12 may be configured to rotate from the first position 16 generally aligned with the longitudinal axis to a second, flip position 20 which is nonparallel with the longitudinal axis 18. The first position 16 may be about 0 degrees. In at least one embodiment, the blade 12 positioned in the second, flip position 20 may be positioned generally orthogonal to the blade 12 in the first position 16. In at least one embodiment, the blade 12 positioned in the second, flip position 20 may be positioned generally 90 degrees to the blade 12 in the first position 16. In other embodiments, the blade 12 in the second, flip position may be positioned at an angle other than 90 degrees.

Figure 20:
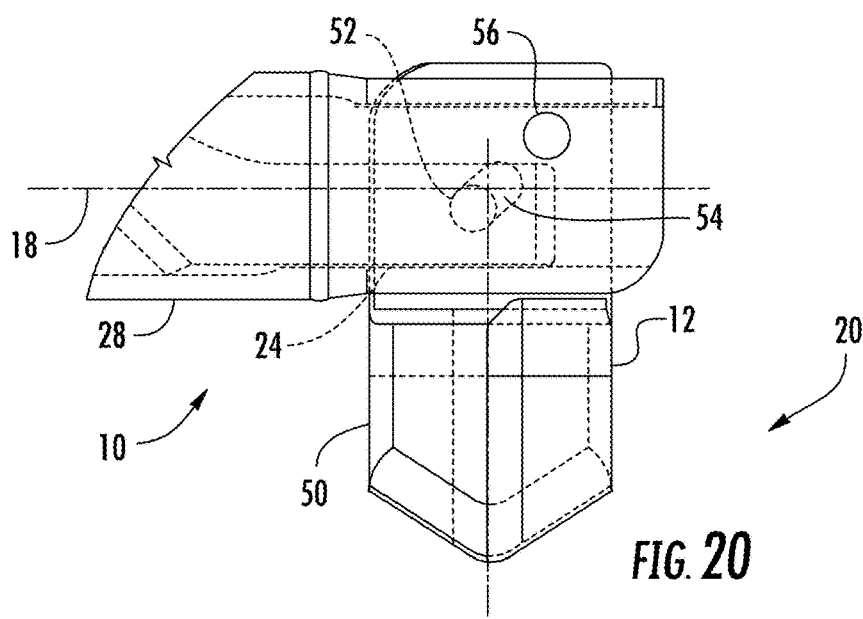
FIG. 20 is a detail side view of the blade in the second position.
Figure 21:
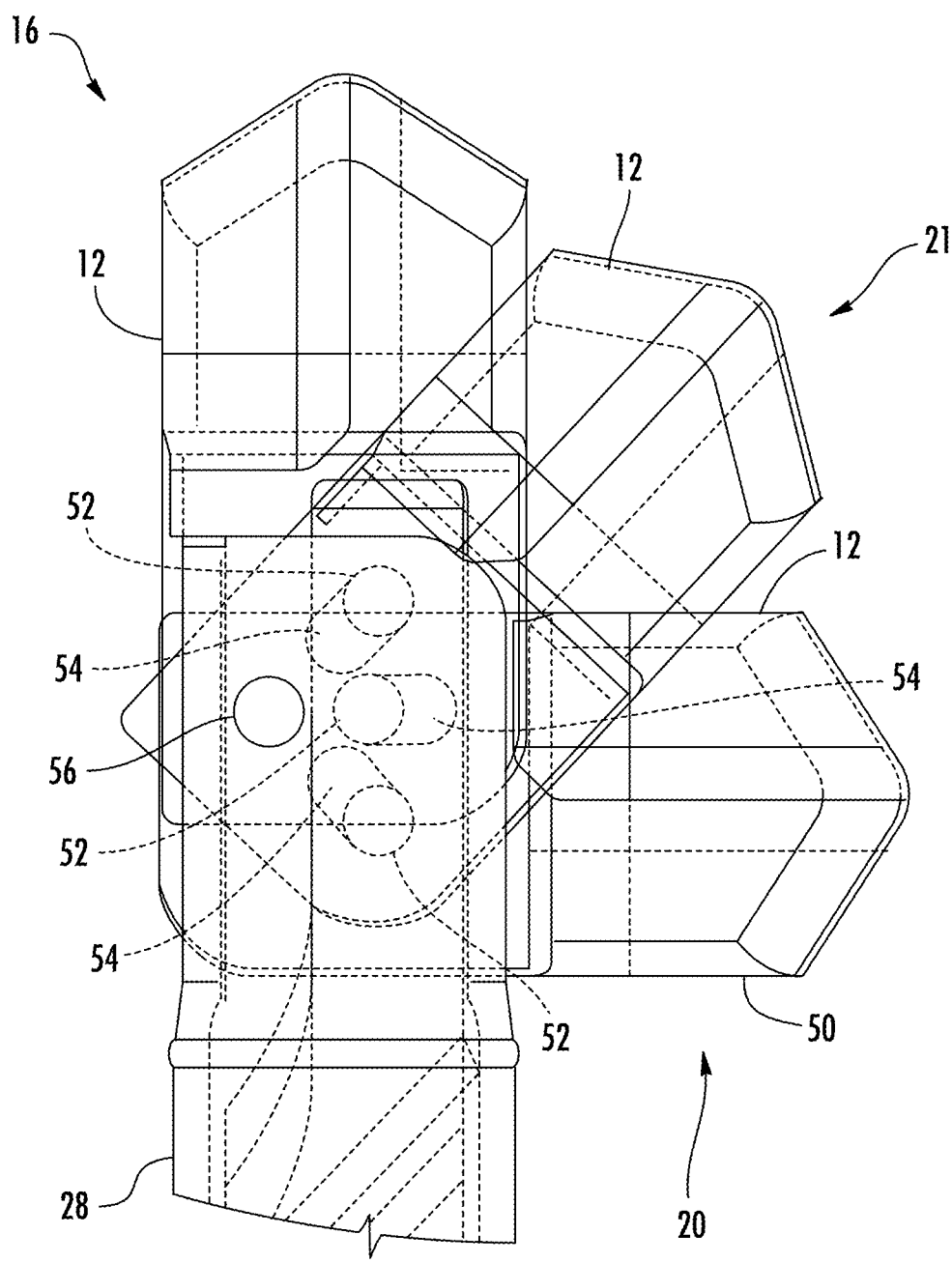
FIG. 21 is a detail compilation side view of the blade in the first position, second position and moving between the first and second positions.
Figure 22:
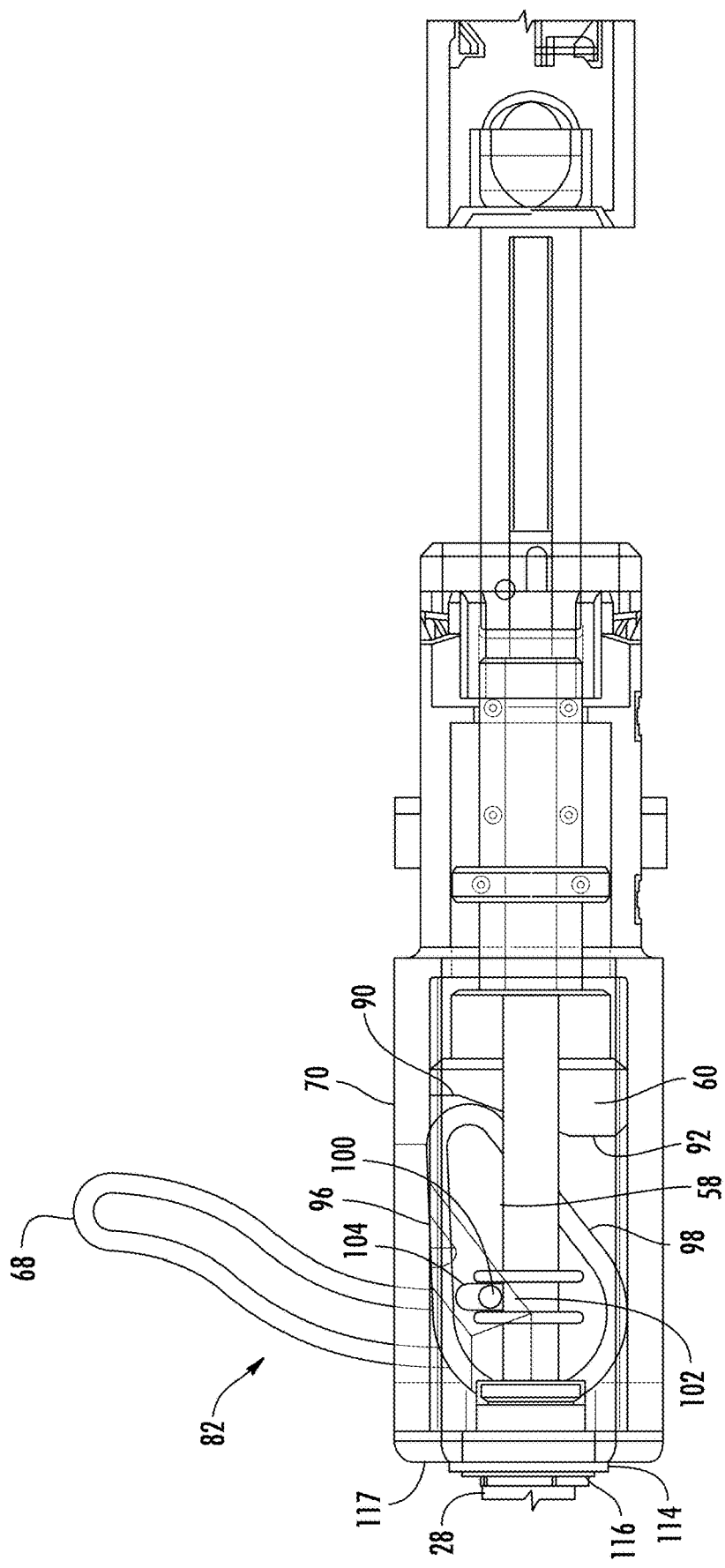
FIG. 22 is a detail view of a proximal end of the device showing the actuation device in the first position.
Figure 23:
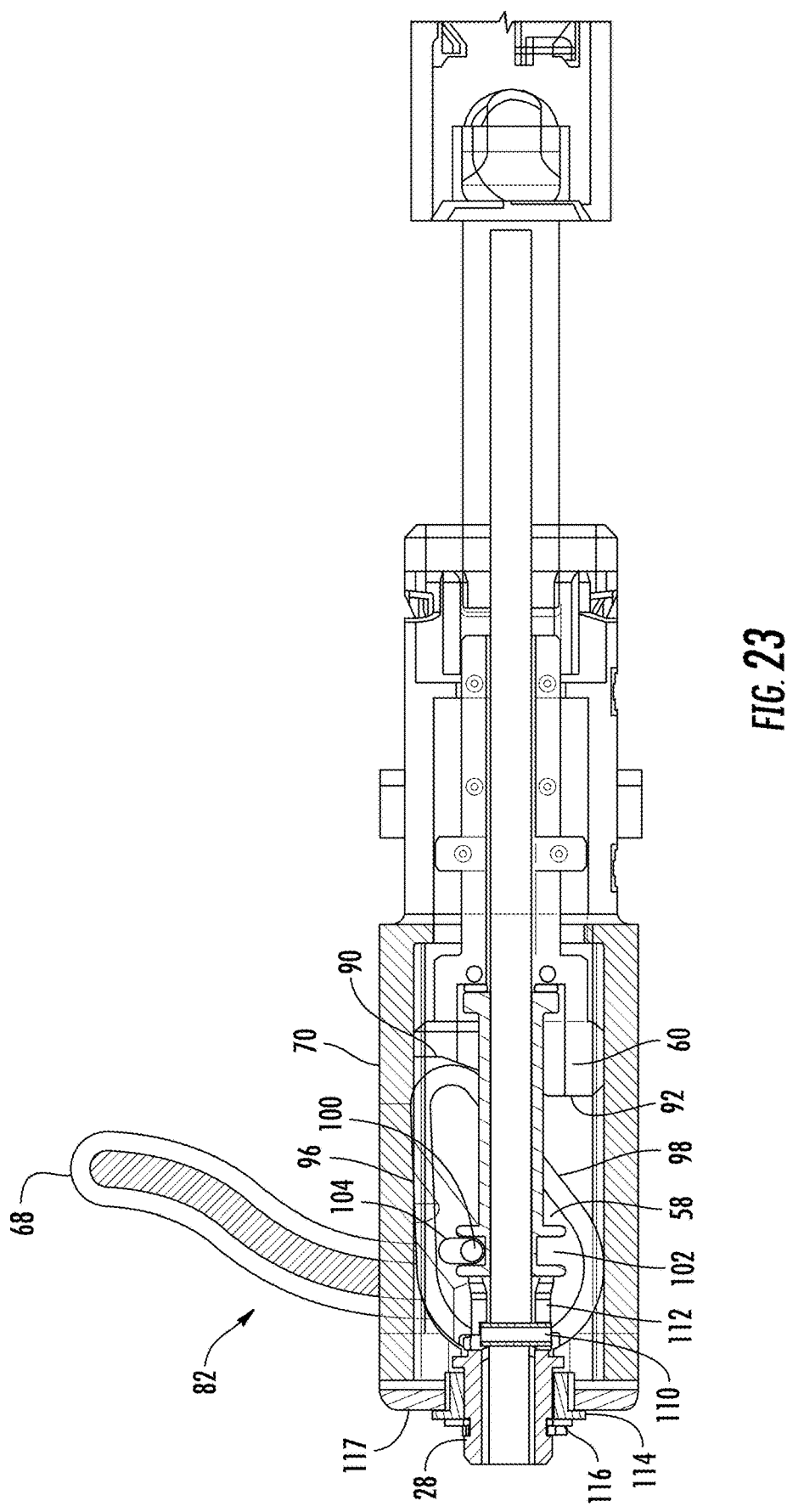
FIG. 23 is a cross-sectional side view of the detail view of FIG. 22.
Figure 24:
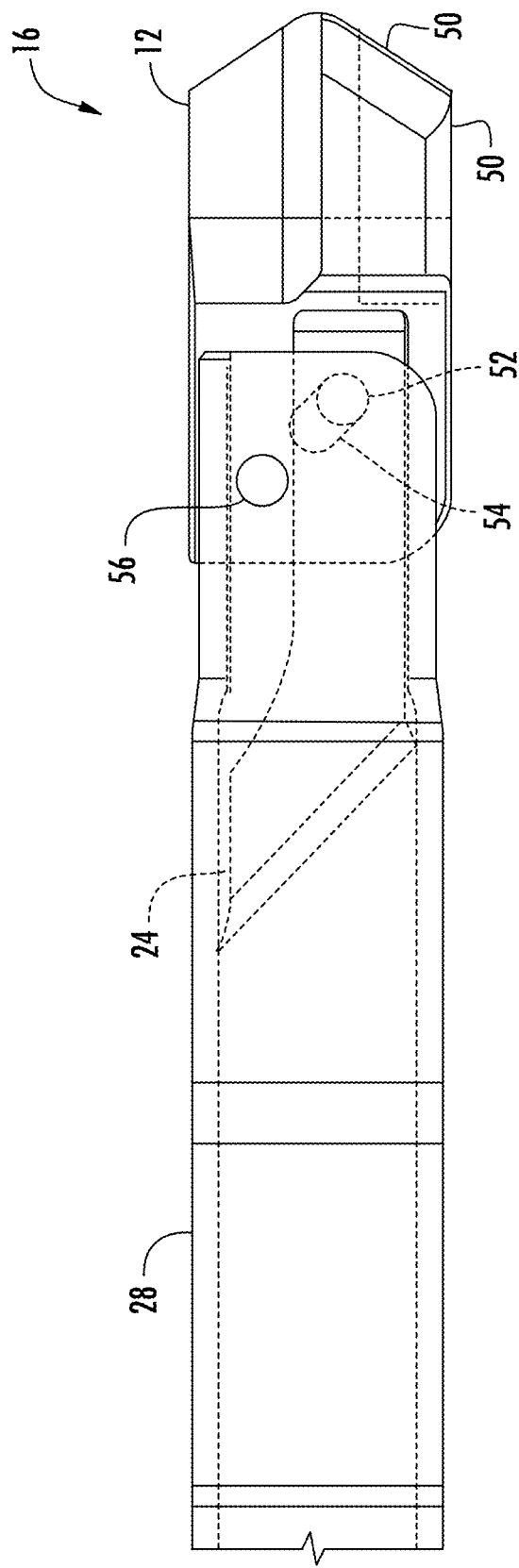
FIG. 24 is a detail side view of the distal end of the device when the actuation device is in the first position shown in FIGS. 22 and 23 and the cam is in contact with a first position retainer on the cam follower.

The blade 12 may have any appropriate configuration that enables the blade 12, when in the first position 16, to be used to drill a hole 30 in bone of a patient and to be used, when in the second position 20, to drill a retrograde socket 32 or tunnel. In at least one embodiment, the blade 12 may include a cutting arris 50 forming a leading edge of the distal tip. The leading edge may be nonparallel and may be nonorthogonal relative to the longitudinal axis of the elongated body 36. In the second position 20, as shown in FIGS. 20 and 21, the cutting arris 50 may be positioned generally orthogonal to the longitudinal axis of the elongated body 36.

Figure 4:
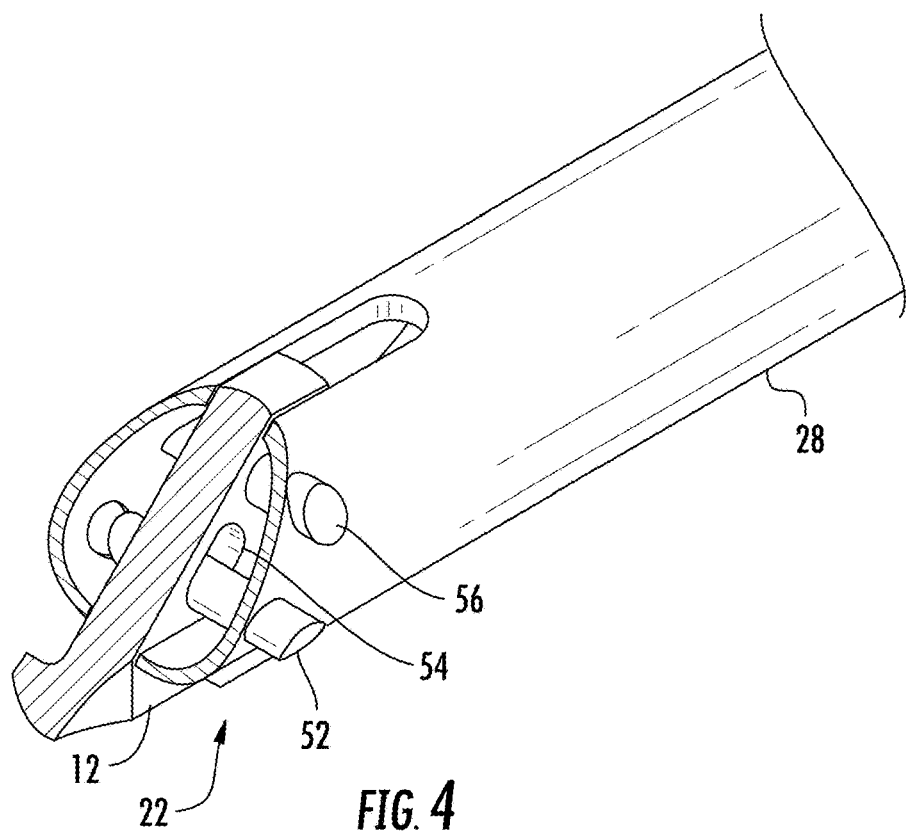
FIG. 4 is a partial cross-sectional perspective view of the blade taken at section line 4-4 in FIG. 1.
Figure 5:
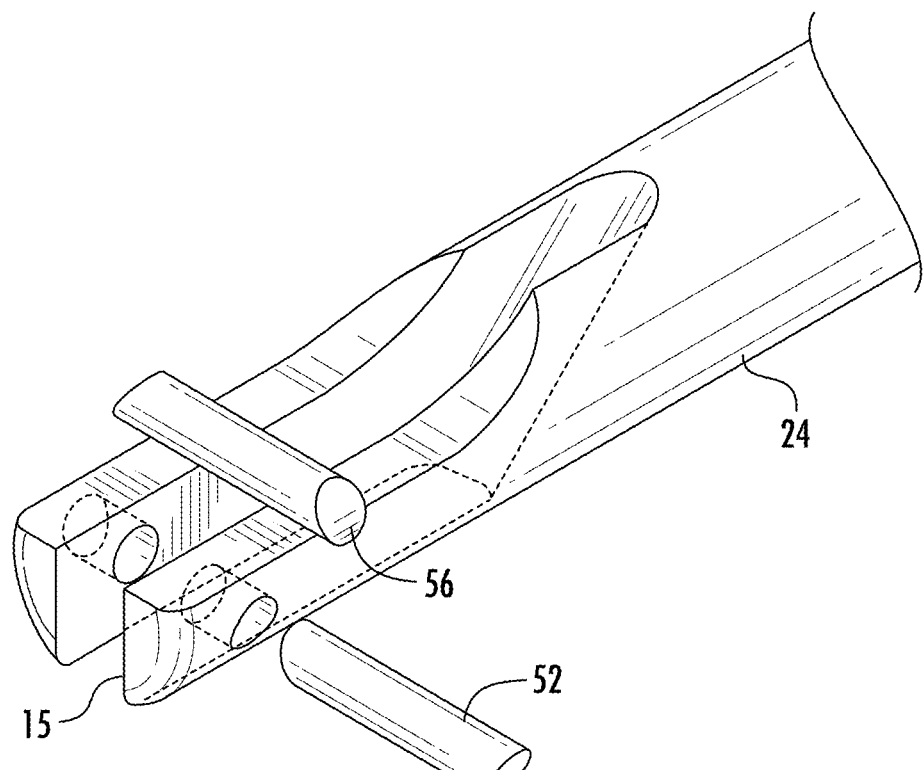
FIG. 5 is a partial perspective view of the distal end of the inner shaft.
Figure 6:
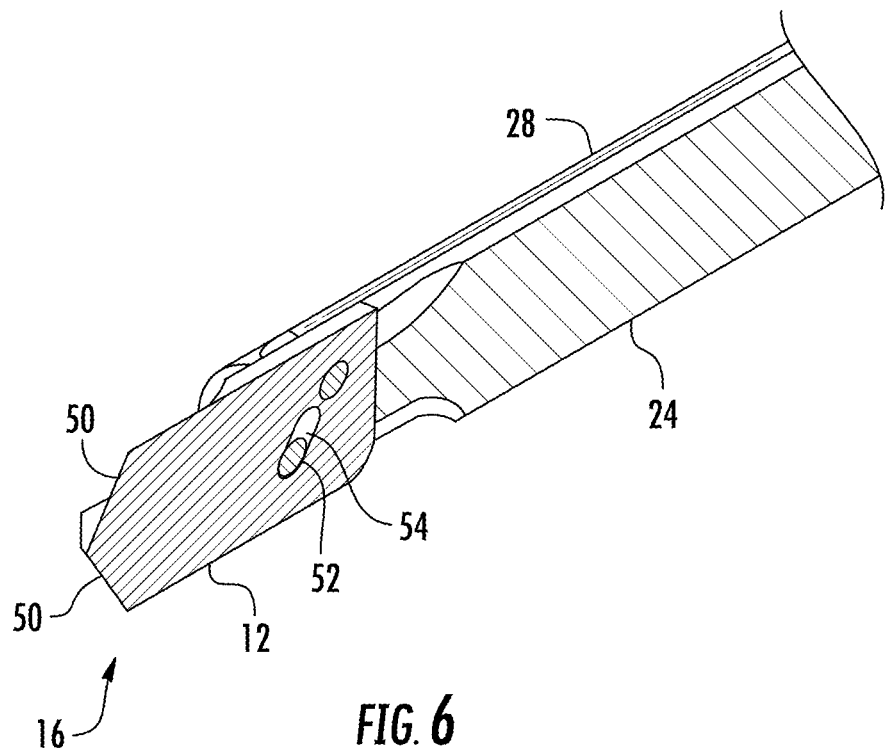
FIG. 6 is a partial cross-sectional view of the distal end of the medical device taken at section line 6-6 in FIG. 1.

The blade position control system 26 may be configured to control position of the blade 12 between the first and second positions 16, 20. In at least one embodiment, the blade position control system 26 may connect the blade 12 to distal ends of both the outer tube 28 and inner shaft 24. The blade position control system 26 may include a connection system 22 connecting the inner shaft 24 to the blade 12 that allows the blade 12 to move from the first position 16 generally aligned with the longitudinal axis 18 to the second, flip position 20 which is nonparallel with the longitudinal axis 18 and whereby a cutting arris 50 of the blade 12 is exposed toward the proximal end 38 of the elongated body 36 for retrograde drilling of a hole 30 when the blade 12 is locked in the second, flip position 20. In at least one embodiment, the connection system 22 connecting the inner shaft 24 to the blade 12 may include a pin 52 and a slot 54 that allow conversion of linear movement of the inner shaft 24 into rotational movement of the blade 12 to rotate the blade 12 to the second, flip position 20 upon linear movement of the inner shaft 24 in relation to the outer tube 28. As shown in FIG. 4, the pin 52 may slide in the slot 54 to permit rotation of the blade 12 about the pivot point 56, which may be a pin or other appropriate device. In at least one embodiment, the pivot point 56 is a point at which the blade 12 is pivotably coupled to the outer tube 28. The blade 12 may partially reside within a distal end of the outer tube 28 and may include two slots 57 configured to enable the blade 12 to be rotated into the second position 20. Such configuration enables the blade to be movable from the first position 16 to the second position 20, and vice versa, via lateral movement of the inner shaft 24. When the inner shaft 24 is moved laterally, the blade 12 may be articulated to a nonparallel second position 20 relative to the longitudinal axis 18 of the elongated body 36 in which the cutting arris 50 of the blade 12 is exposed toward the proximal end 38 of the elongated body 36 for retrograde drilling of a hole 30 when the blade 12 is locked in the second, flip position 20.

Figure 7:
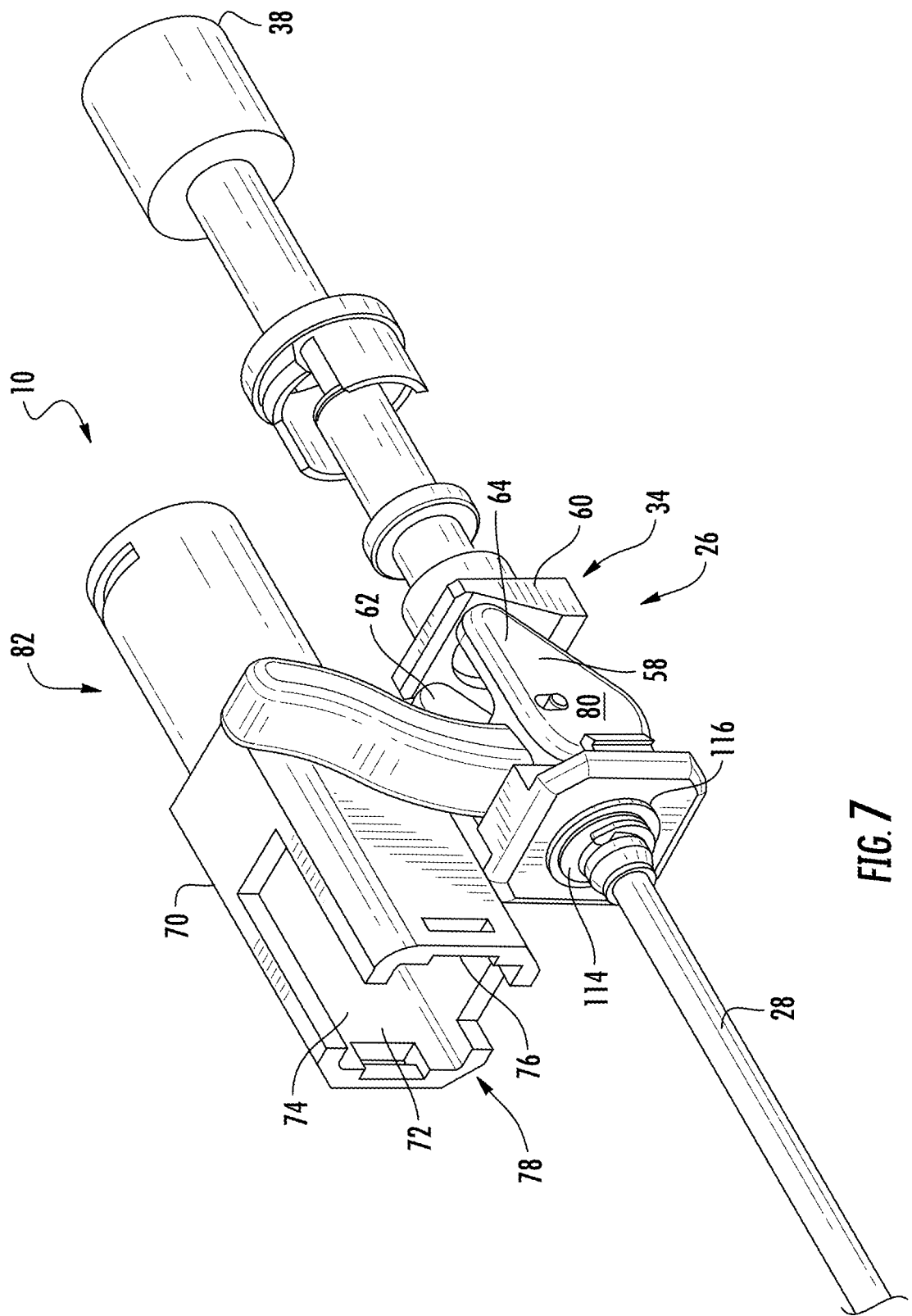
FIG. 7 is a partially exploded, perspective view detail of the proximal end of the medical device taken at section line 7-7 in FIG. 1.
Figure 8:
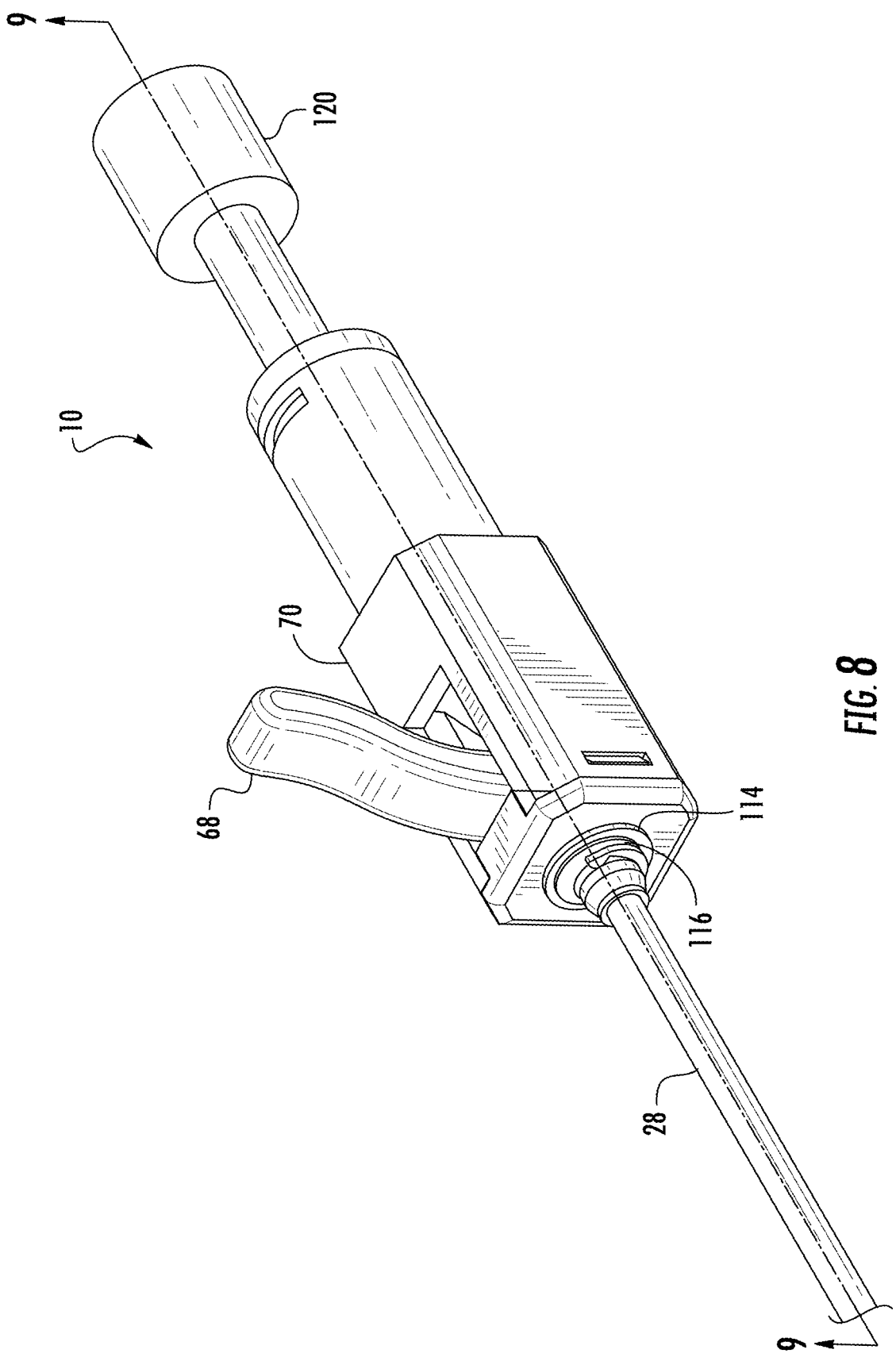
FIG. 8 is a perspective view detail of the proximal end of the medical device taken at section line 7-7 in FIG. 1.
Figure 25:
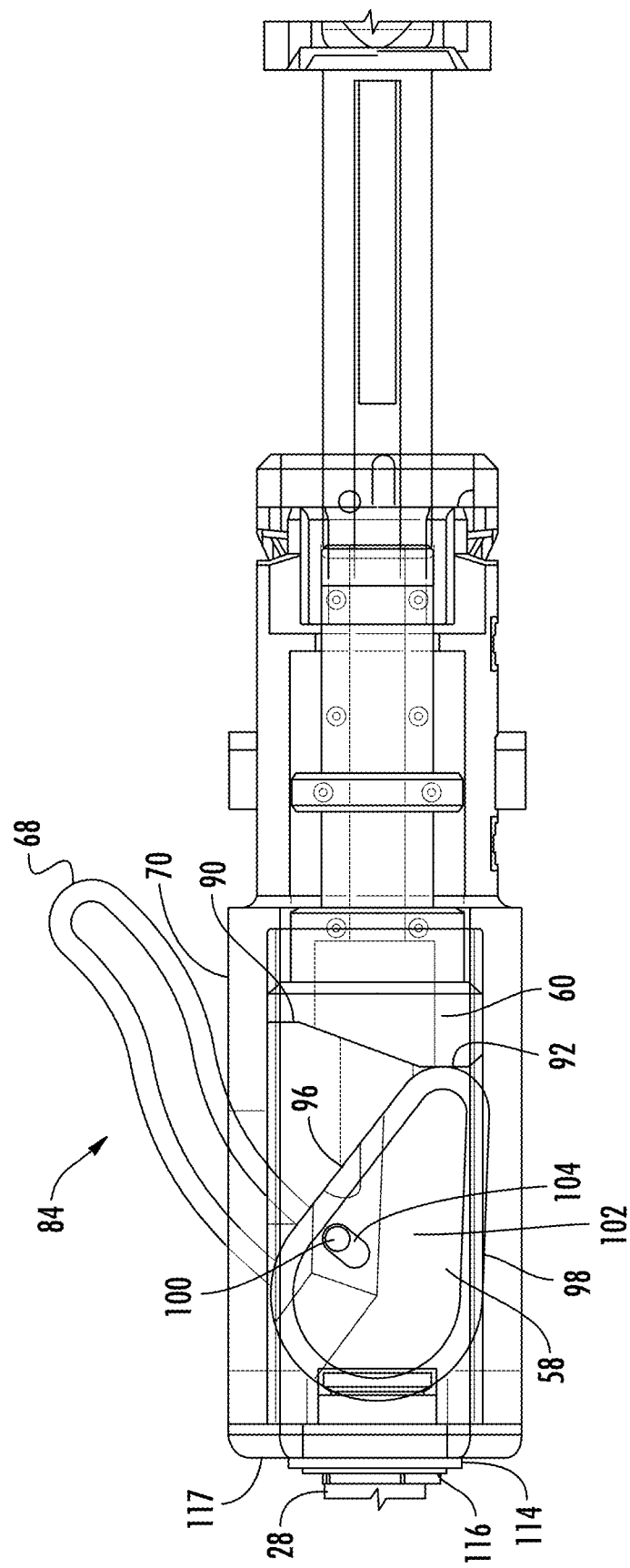
FIG. 25 is a detail view of a proximal end of the device showing the actuation device in the second position.
Figure 26:
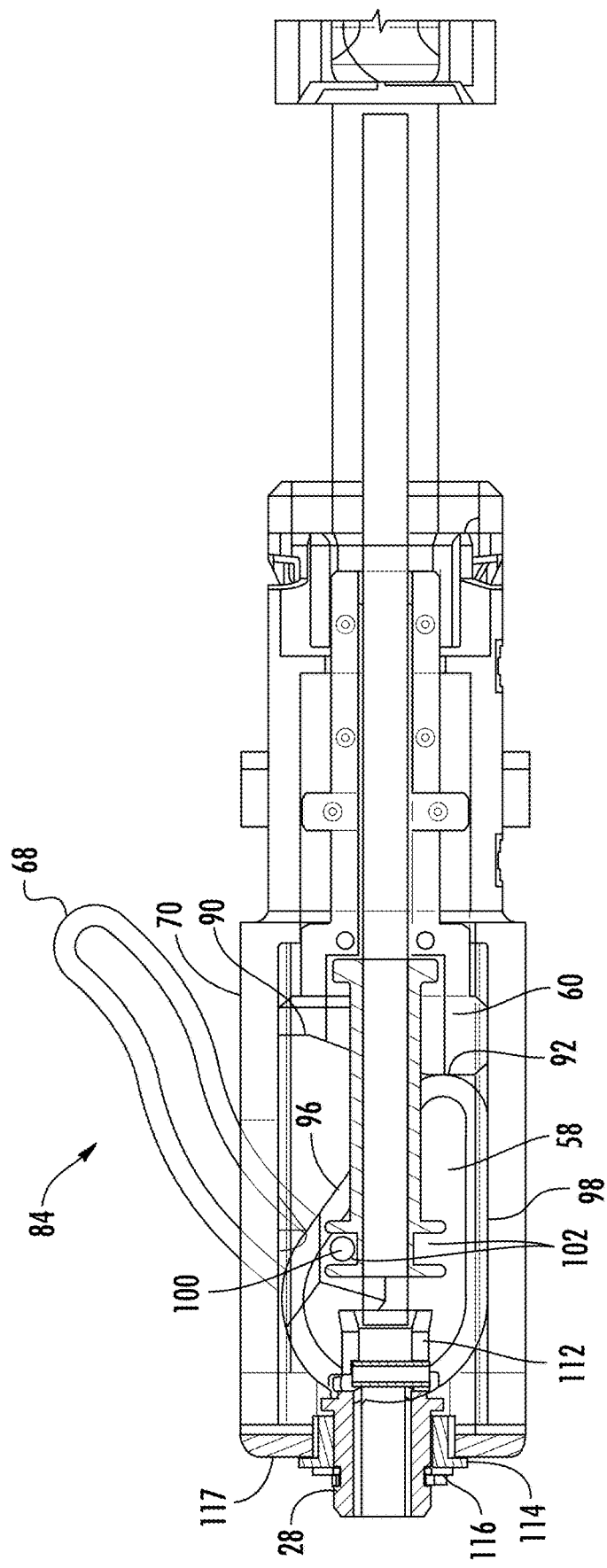
FIG. 26 is a cross-sectional side view of the detail view of FIG. 25.
Figure 27:
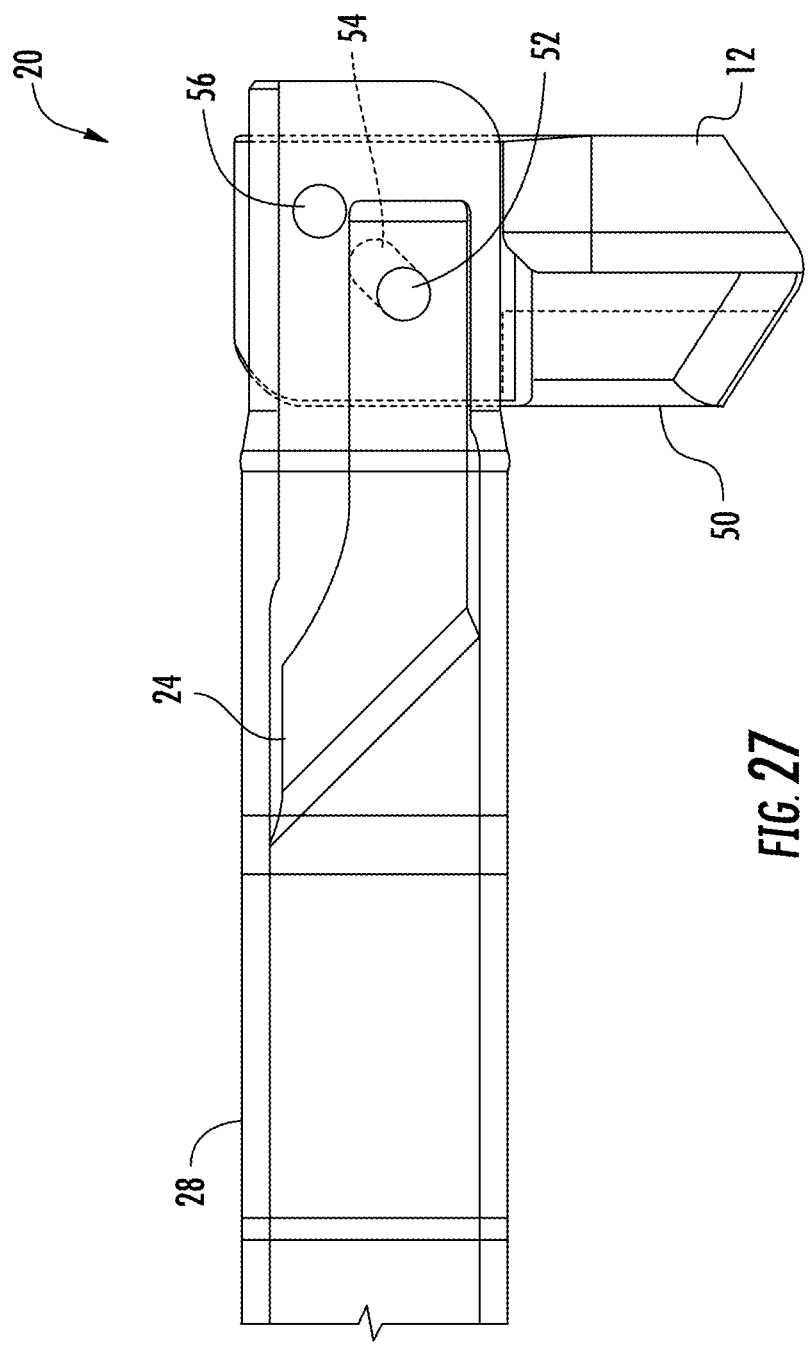
FIG. 27 is a detail side view of the distal end of the device when the actuation device is in the second position shown in FIGS. 25 and 26 and the cam is in contact with a second position retainer on the cam follower.

The blade position control system 26 may include one or more cams 58 in communication with a cam follower 60 that is in communication with the inner shaft 24 for moving the blade 12 into first and second positions 16, 20. In at least one embodiment, the cam 58 may be formed from a first head member 62 and a second head member 64 separated by a tube receiving chamber 66 configured to receive the inner shaft 24 extending therethrough. By straddling the inner shaft 24, the inner shaft 24 provides stability and resistant to torque placed on the cam 58 by an actuation device 68, which may be, but is not limited to being a lever arm, extending from the cam 58. The blade position control system 26 may include a housing 70 configured to retain the cam 58 in position whereby the housing 70 may include an inner side surface 72 that houses the cam 58 to prevent the cam 58 from being inadvertently displaced and to limit rotation of the cam 58 to rotate about only one axis. In at least one embodiment, as shown in FIG. 7, the housing 70 may include a first inner side surface 74 and a second inner side surface 76 that face each other and partially define a cam receiving cavity 78 configured such that the housing 70 limits movement of the cam 58 such that the cam 58 can only move with outer side surfaces 80 of the cam 58 moving in a direction generally aligned with first and second inner side surfaces 74, 76 of the housing 70. In particular, the housing 70 limits movement of the cam 58 between a first position 82, as shown in FIG. 7, with the actuation device 68 extending radially away from the housing 70 and a second position 84, as shown in FIGS. 25 and 26, in which the actuation device 68 may be generally aligned with the outer tube 28.

The cam 58 may also be configured to prevent over rotation of the cam 58. In particular, the cam 58 may include a first side edge 96 that is configured to prevent over rotation of the cam 58. In particular, the first side edge 96 of the cam 58 may be generally aligned with an inner surface 71 of the housing 70 when the cam 58 is in the first position 82. Similarly, the cam 58 may include a second side edge 98 that is configured to prevent over rotation of the cam 58. In particular, the second side edge 98 of the cam 58 may be generally aligned with an inner surface 73 of the housing 70 when the cam 58 is in the second position 84.

The cam follower 60 may include a first position retainer 86, as shown in FIGS. 30-33, configured to retain the cam 58 in the first position 82, which also retains the blade 12 in a position generally aligned with the longitudinal axis 18, and a second position retainer 88 configured to retain the cam 58 in the second position 84 in which the cutting arris 50 of the blade 12 is positioned such that the cutting arris 50 is exposed toward the proximal end 38 of the elongated body 36 for retrograde drilling of a hole 30 while allowing the inner shaft 24 and blade 12 to rotate. In at least one embodiment, the first position retainer 86 may be formed from a nonlinear engaging surface 94 with a flat surface 90 generally orthogonal to the longitudinal axis 18 of the elongated body 36, which also retains the blade 12 in a position generally aligned with the longitudinal axis 18. The second position retainer 90 may be formed from a flat surface 92 generally orthogonal to the longitudinal axis 18 of the elongated body 36. The second position retainer may be positioned closer to the distal end 14 of the elongated body 36 than the first position retainer 86. The engaging surface 94 of the cam follower 60 between the first and second position retainers 86, 88 is nonorthogonal relative to the longitudinal axis 18 of the elongated body 36.

Figure 18:
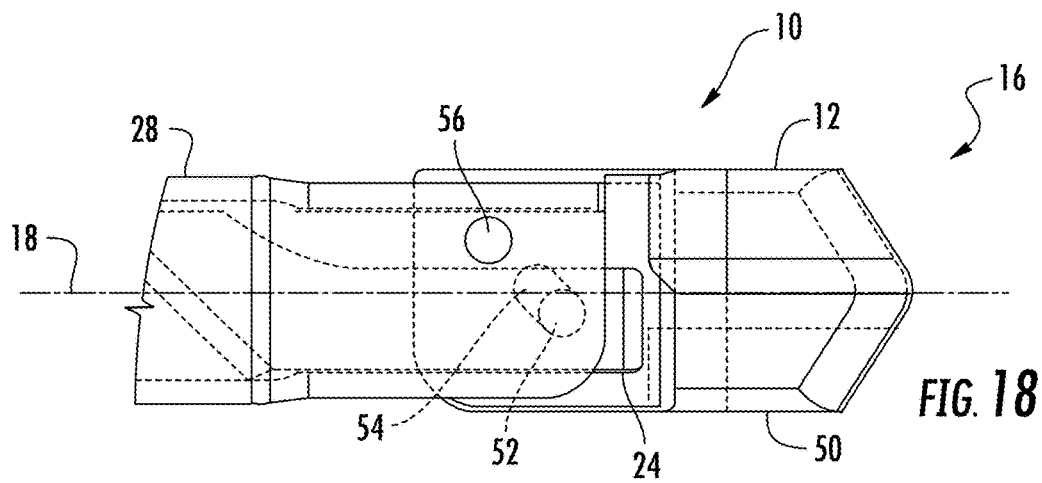
FIG. 18 is a detail side view of the blade in the first position.
Figure 19:
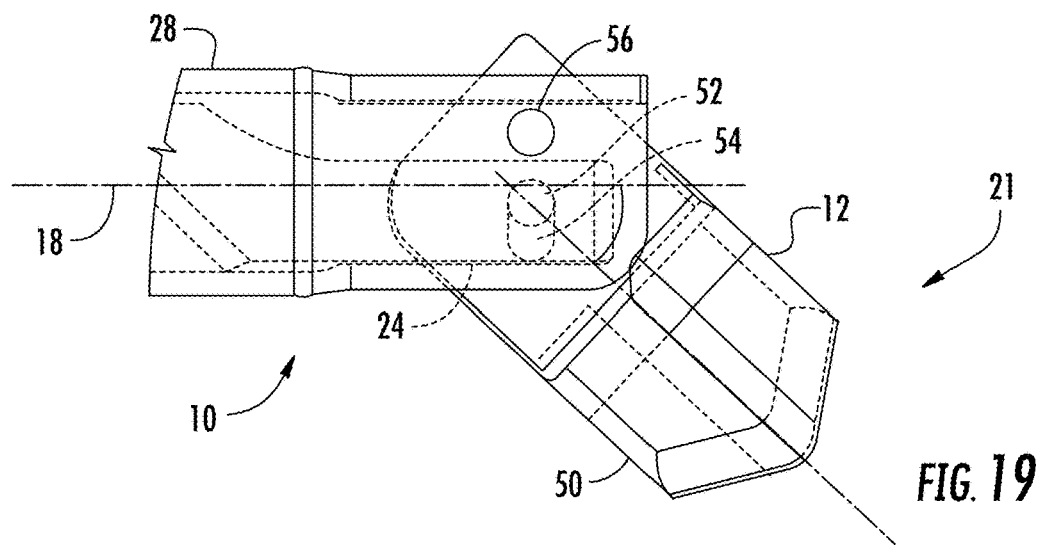
FIG. 19 is a detail side view of the blade moving between the first and second positions.
Figure 28:
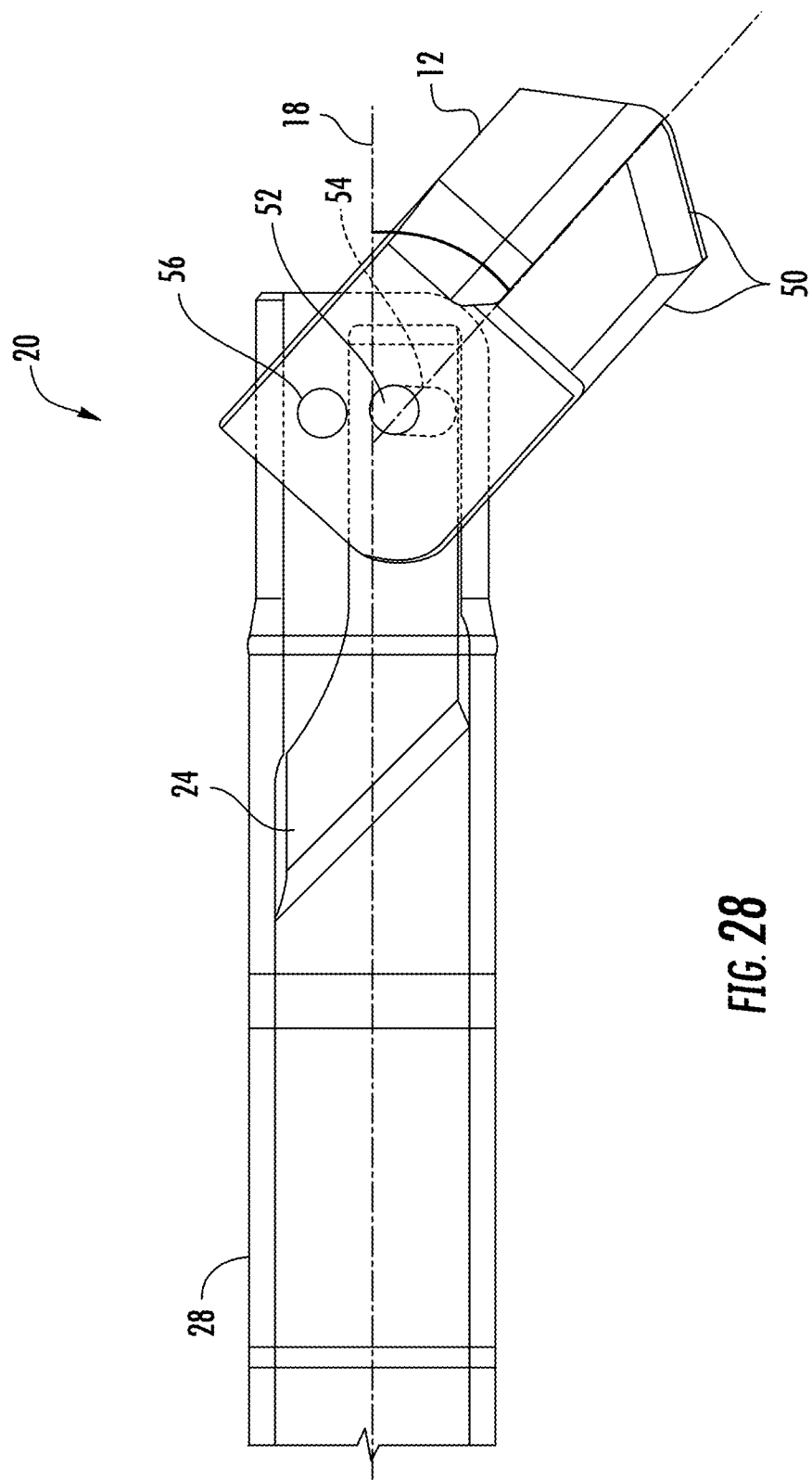
FIG. 28 is a detail side view of the distal end of the device with the blade at about 45 degrees when the cam is in contact with a third position retainer on the cam follower and the actuation device is positioned in between the first and second position shown in FIGS. 24 and 27.
Figure 29:
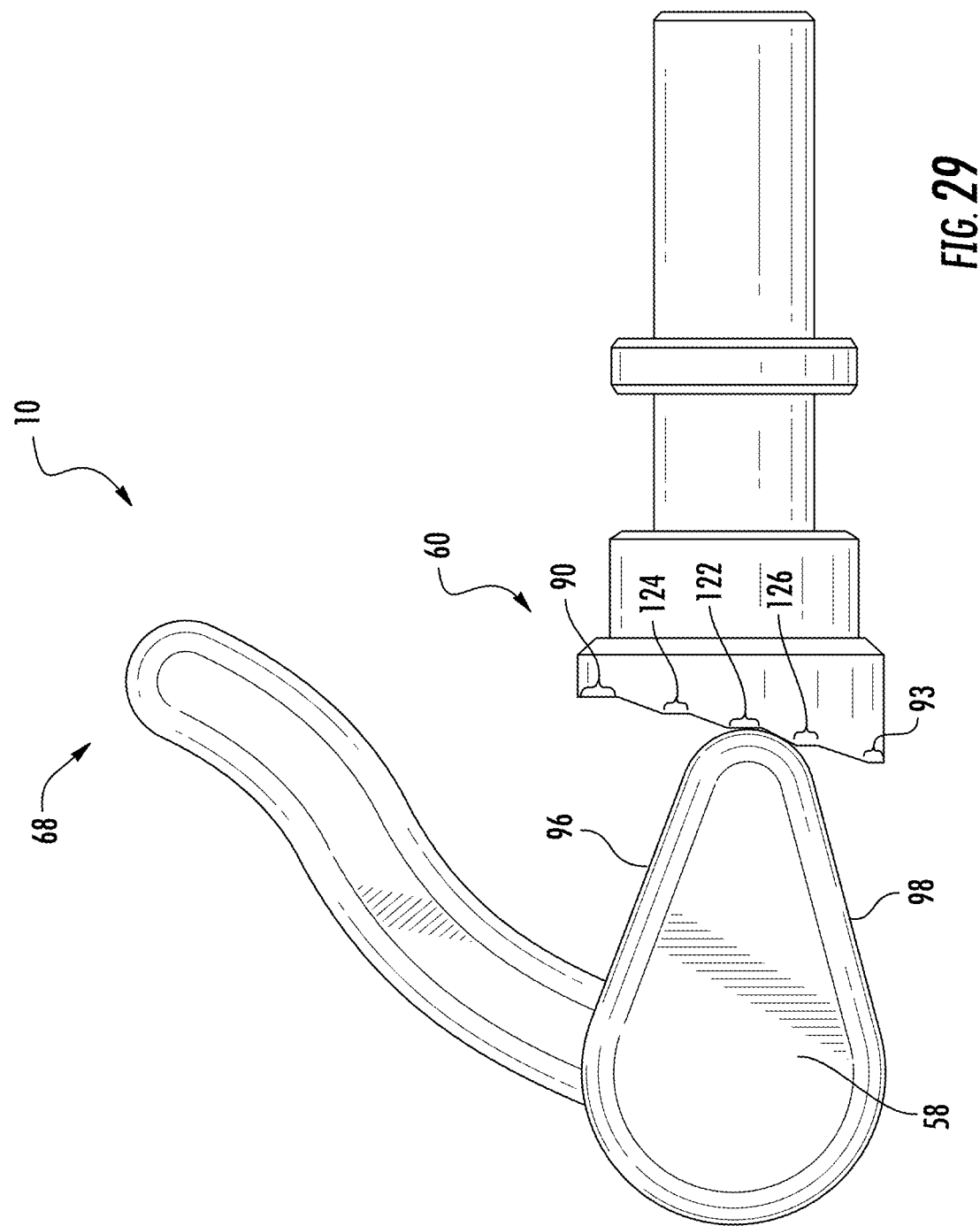
FIG. 29 is a detail side view of the cam and cam follower with the cam in contact with a third position retainer on the cam follower when the blade at the distal end of the device is at about 45 degrees.
Figure 30:
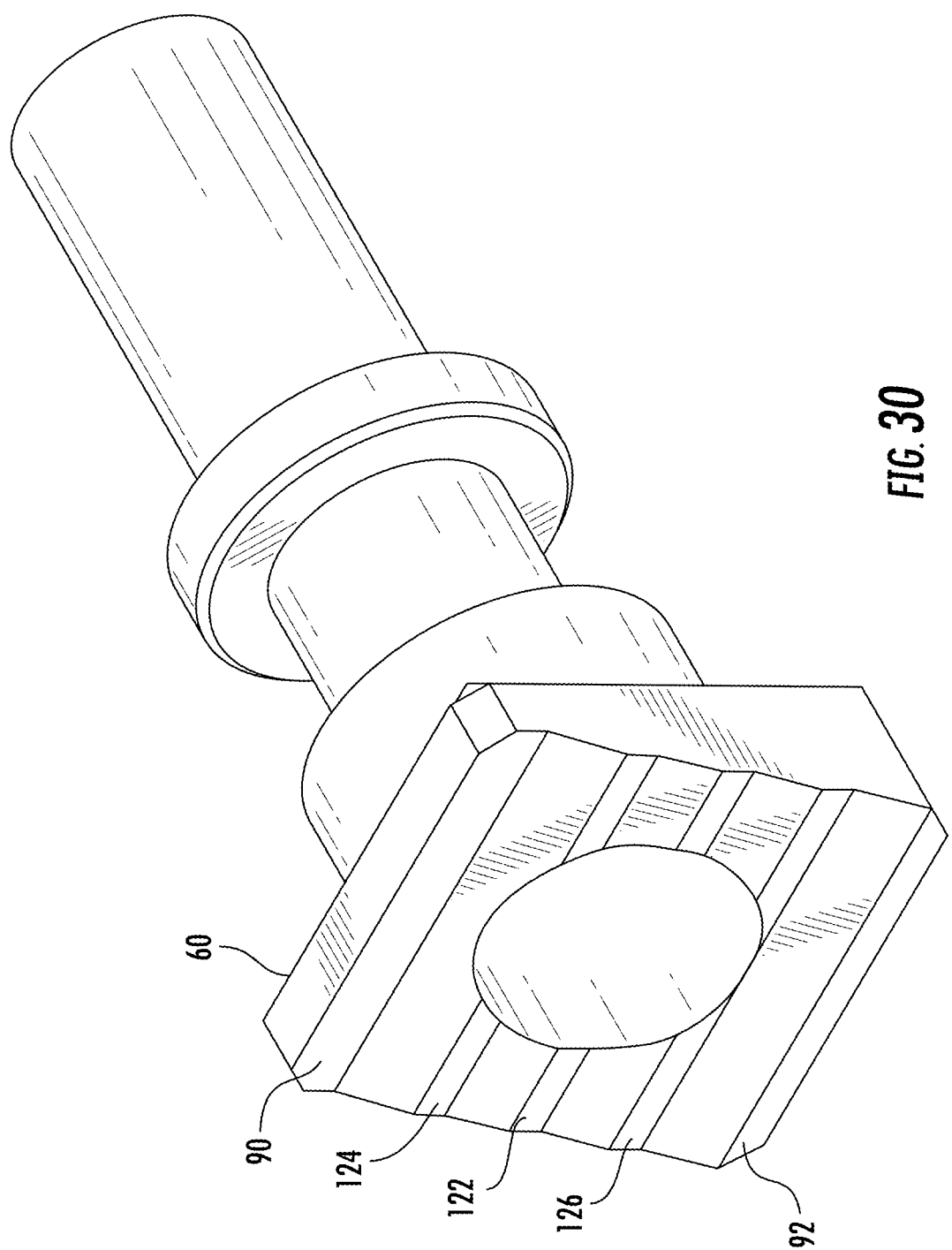
FIG. 30 is a perspective view of another embodiment of the cam follower including first, second, third, fourth and fifth position retainers.
Figure 31:
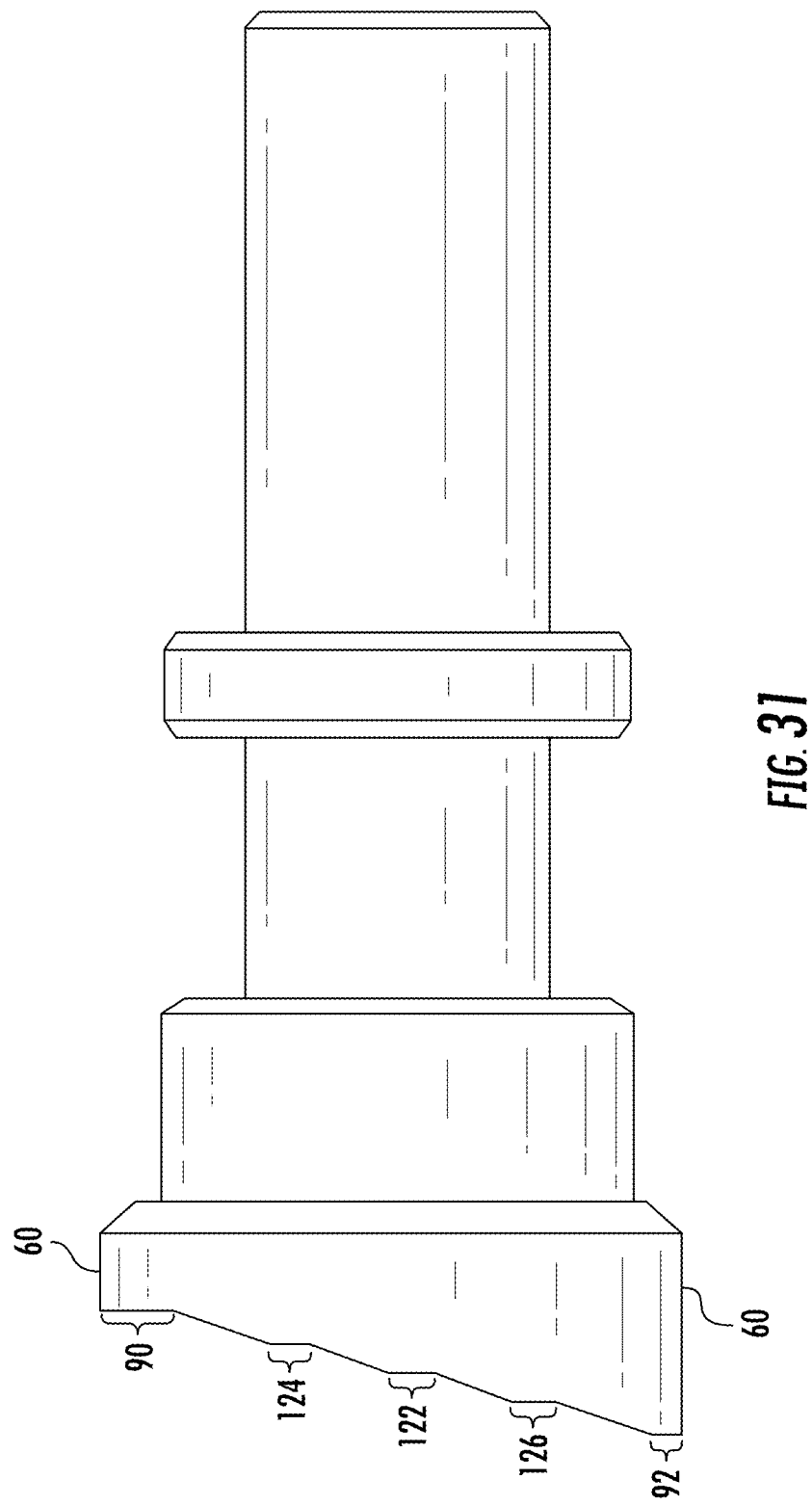
FIG. 31 is a side view of another embodiment of the cam follower shown in FIG. 29 including first, second, third, fourth and fifth position retainers.

In at least one embodiment, the device 10 may include at least one additional position for the blade 12 between the first and second positions 16, 20, as shown in FIGS. 30-36. In particular, the blade 12 may be retained in a desired position somewhere between being aligned with the longitudinal axis 18, as shown in FIG. 18, and generally orthogonal to the longitudinal axis 18, as shown in FIG. 20. For example, the device 10 may be configured such that the blade 12 may be retained in a third position 21, as shown in FIGS. 19 and 21. The third position 21 may be in any desired position. In at least one embodiment, the third position 21 may be about halfway between the first and second positions 16, 20, as shown in FIGS. 30-33. In at least one embodiment, as shown in FIG. 28, the third position may be positioned at about 45 degrees relative to the longitudinal axis 18. The blade 12 may be retained in the third position 21 via a third position retainer 121, as shown in FIG. 29, positioned between the first and second position retainers 86, 88 for retaining the cam 58 in a third position in which the blade 12 is positioned between the first and second positions. In at least one embodiment, the third position retainer 121 may be, but is not limited to being, a flat surface 122 on the cam follower 60 that is positioned about midway between the flat surface 90, which corresponds to the first position 16 of the blade 12, and the flat surface 92, which corresponds to the second position 20 of the blade 12. The third position 21 enables a user of the device 10, such as a surgeon, to create compound sockets, counterbores and countersinks within bone.

Figure 32:
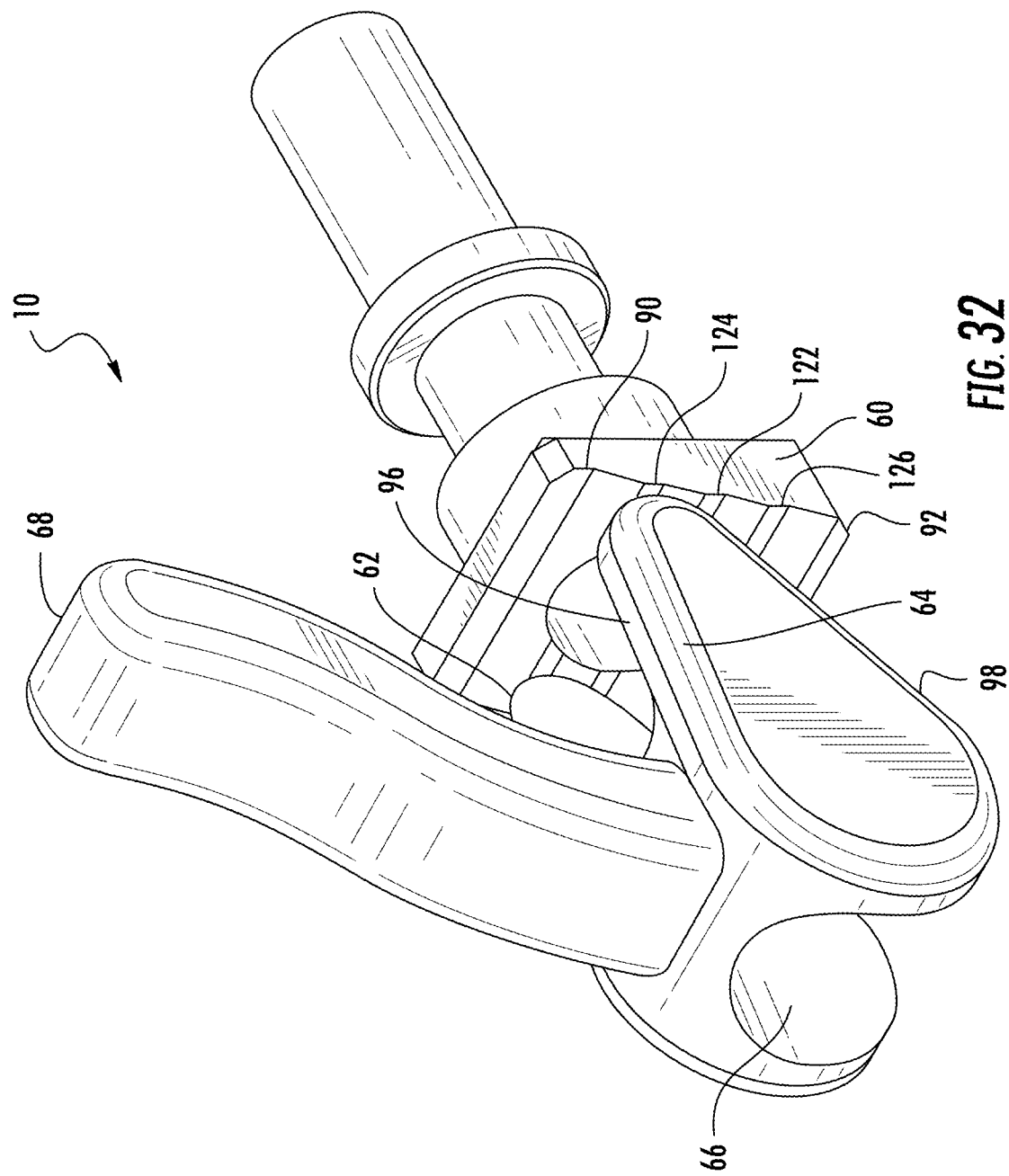
FIG. 32 a perspective view of the cam in contact with a fourth position retainer on the cam follower.
Figure 33:
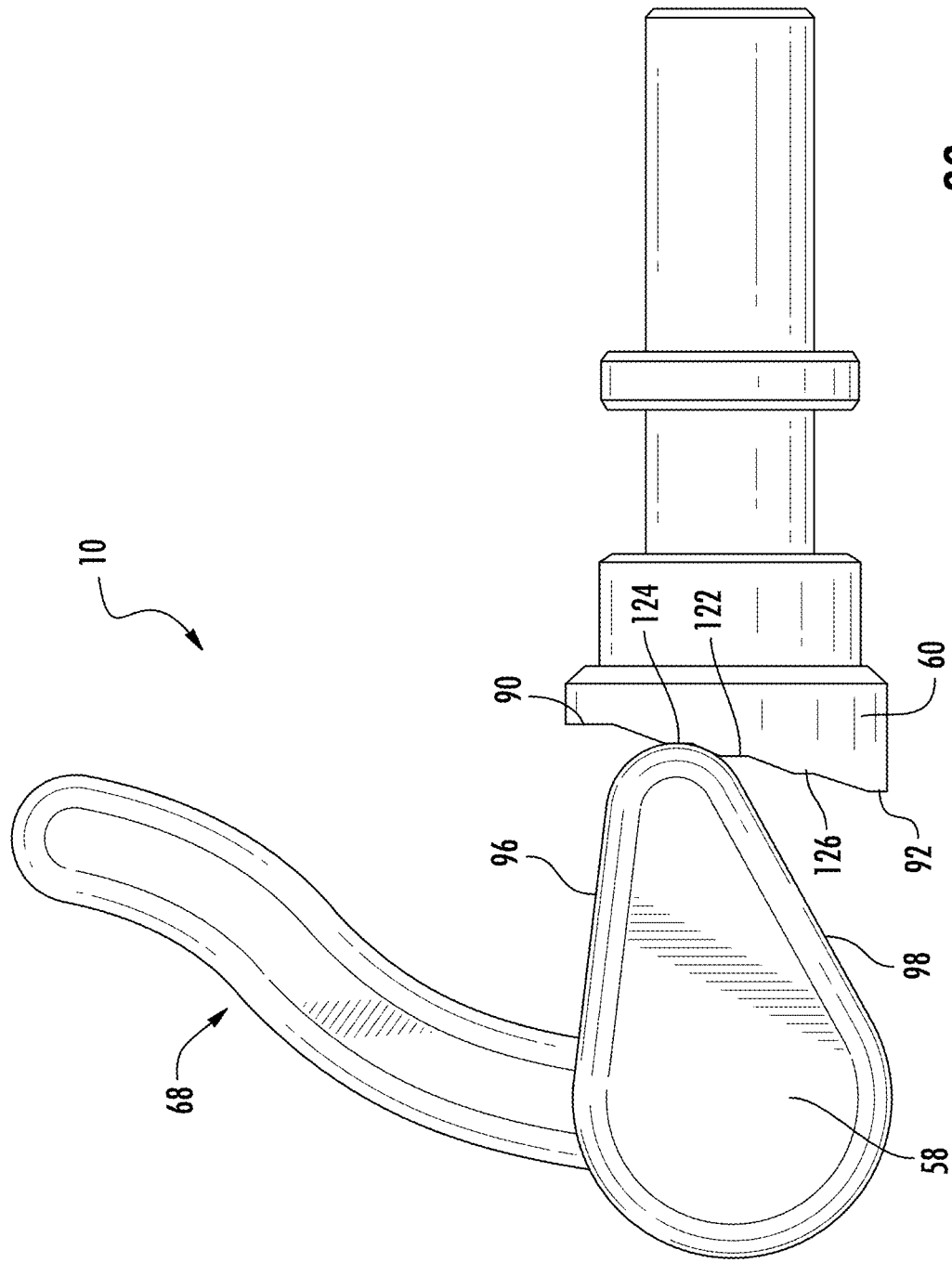
FIG. 33 is a side view of the cam in contact with a fourth position retainer on the cam follower.
Figure 34:
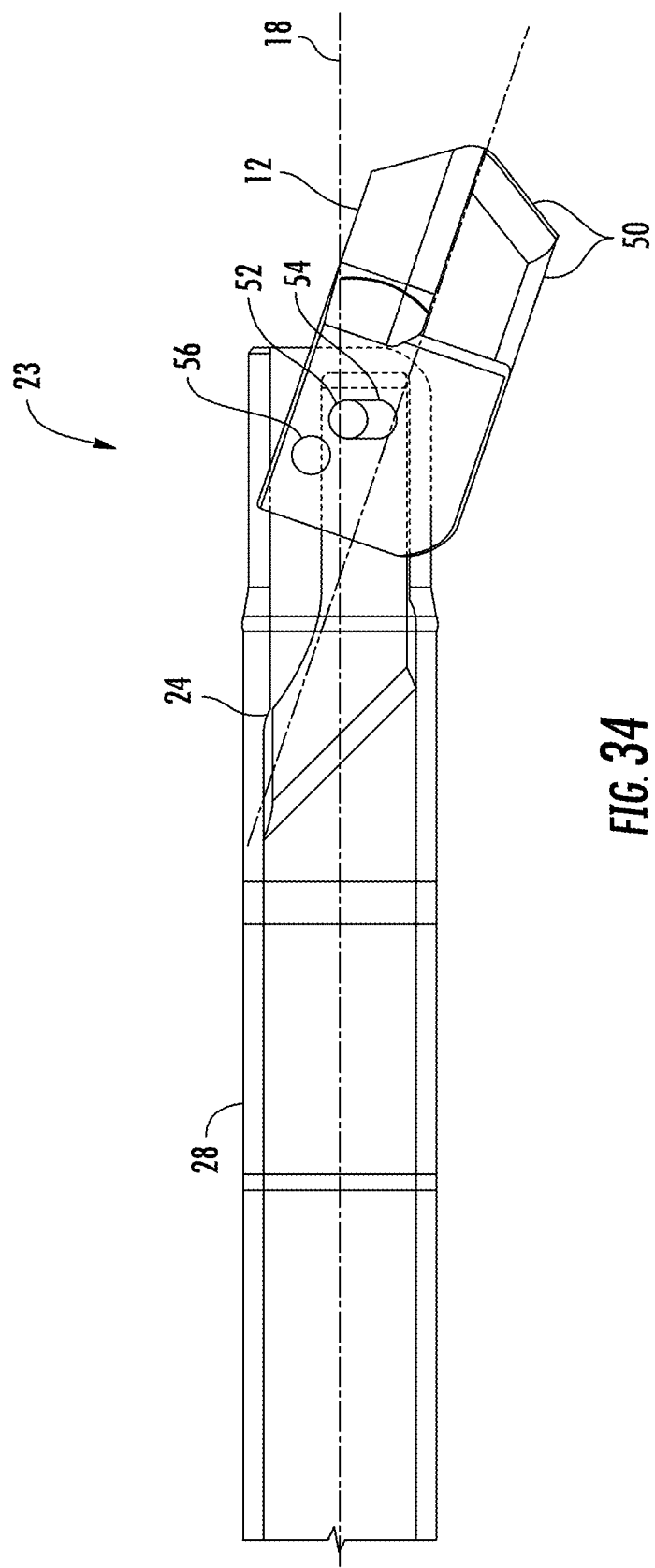
FIG. 34 is a detail side view of the distal end of the device with the blade in a fourth position at about 30 degrees when the cam is in contact with a fourth position retainer on the cam follower and the actuation device is positioned in between the first and third positions.

The device 10 may include additional positions for the blade 12 between the first and third positions 16, 21 and between the second and third positions 20, 21, as shown in FIGS. 30-36. In at least one embodiment, the cam 58 may be retained in a fourth position, as shown in FIGS. 32 and 33, between the first and third positions via a fourth position retainer 123 positioned between the first and third position retainers 88, 121. In at least one embodiment, the fourth position retainer 123 may be, but is not limited to being, a flat surface 124 on the cam follower 60 that is positioned between the flat surface 90, which corresponds to the first position 16 of the blade 12, and the flat surface 121, which corresponds to the third position 21 of the blade 12. The fourth position retainer 123 may be positioned at any point between the first and third position retainers 86, 121. In at least one embodiment, the fourth position retainer 123 may be positioned between the first position retainer 86 and the second position retainer 88, which corresponds to a fourth blade position 23 of between about 10 degrees and 40 degrees and, in at least one embodiment, 30 degrees, as shown in FIG. 34.

Figure 35:
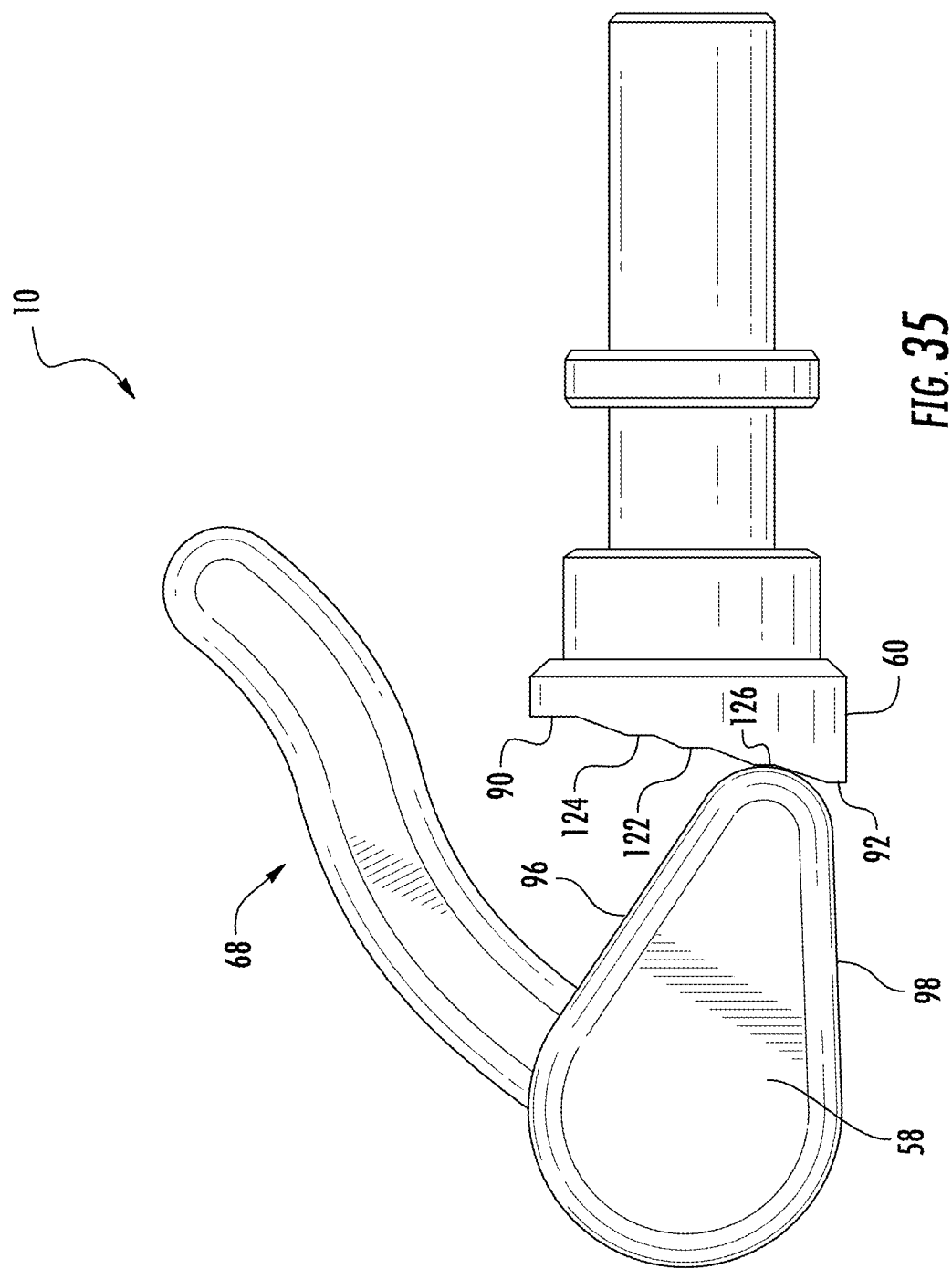
FIG. 35 is a side view of the cam in contact with a fifth position retainer on the cam follower.
Figure 36:
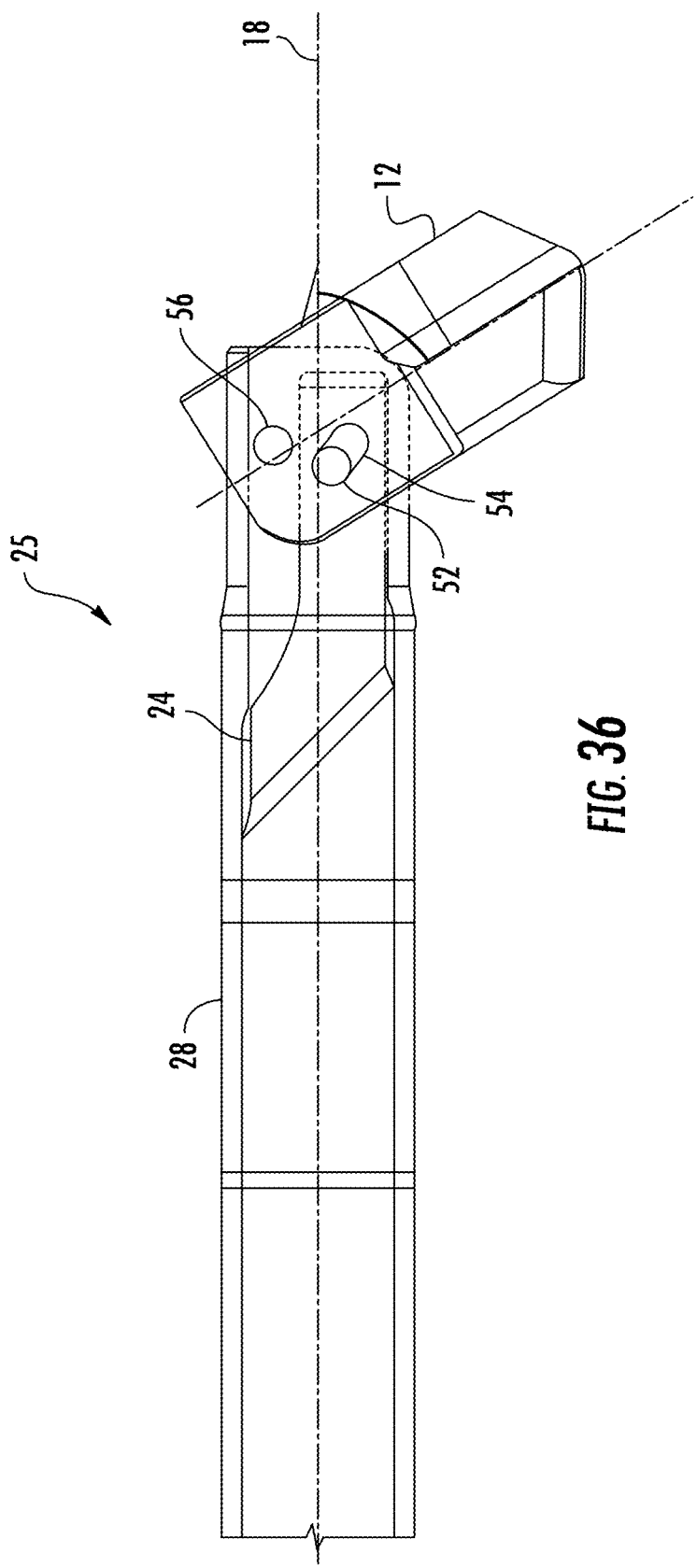
FIG. 36 is a detail side view of the distal end of the device with the blade in a fifth position at about 60 degrees when the cam is in contact with a fifth position retainer on the cam follower and the actuation device is positioned in between the second and third positions.

In at least one embodiment, the cam 58 may be retained in a fifth position, as shown in FIG. 35, between the second and third positions via a fifth position retainer 125 positioned between the second and third position retainers 88, 121. In at least one embodiment, the fifth position retainer 125 may be, but is not limited to being, a flat surface 126 on the cam follower 60 that is positioned between the flat surface 92, which corresponds to the second position 20 of the blade 12, and the flat surface 121, which corresponds to the third position 21 of the blade 12. The fifth position retainer 125 may be positioned at any point between the second and third position retainers 88, 121. In at least one embodiment, the fifth position retainer 125 may be positioned between the second position retainer 88 and the third position retainer 121, which corresponds to a fifth blade position of between about 50 degrees and 80 degrees and, in at least one embodiment, 60 degrees, as shown in FIG. 36.

During use, a user, such as, but not limited to, a surgeon, may cut bone with the blade 12 in any of the positions previously described. The user may create a counterbore by first cutting bone with the blade 12. The user may then move the blade 12 into a position in which the blade 12 is more closely aligned with the first position 16 and the longitudinal axis 18. The remaining hole may be created with the blade 12 more closely aligned with the first position 16 and the longitudinal axis 18. The user may adjust the axial movement of the inner shaft 24 by controlling the position of the cam 58 in contact with the cam follower 60 to produce holes with varying degrees of counter sink at the bottom of the hole.

The user may also vary the position of the blade 12 to create holes with varying diameter by axially moving the inner shaft 24, thereby controlling the position of the cam 58 in contact with the cam follower 60 to create holes with varying diameters. For instance, a 5 mm blade may produce 10 mm hole when flipped at 90 degrees in the second position 20. The same 5 mm blade flipped at 30 degrees (corresponding to flat surface 124 on the cam follower 60) or flipped at 45 degrees (corresponding to flat surface 122 on the cam follower 60) could produce holes less than 10 mm in diameter. The position of the cam 58 may be changed relative to the cam follower 60 via the lever arm 68.

The blade position control system 26 may include a position retention system 34 configured to retain the cam 58 in a second position 84 such that the inner shaft 24 is retained in the second position 20, thereby retaining the cutting arris 50 of the blade 12 in position such that the cutting arris 50 is exposed toward the proximal end 38 of the elongated body 36 for retrograde drilling of a hole 30 while allowing the inner shaft 24 and blade 12 to rotate. The position retention system 34 may include one or more pins 100 extending from the cam 58. The position retention system 34 may include one or more grooves 102 on the inner shaft 24 for receiving the pin 100 extending from the cam 58 such that the inner shaft 24 is rotatable while the pin 100 resides in the groove 102 on the inner shaft 24, thereby preventing axial movement of the inner shaft 24. The position retention system 34 may include one or more slots 104 in the cam 58 for receiving the pin 100 to account for potential misalignment between the pin 100, cam 58 and the groove 102 on the inner shaft 24.

Figure 9:
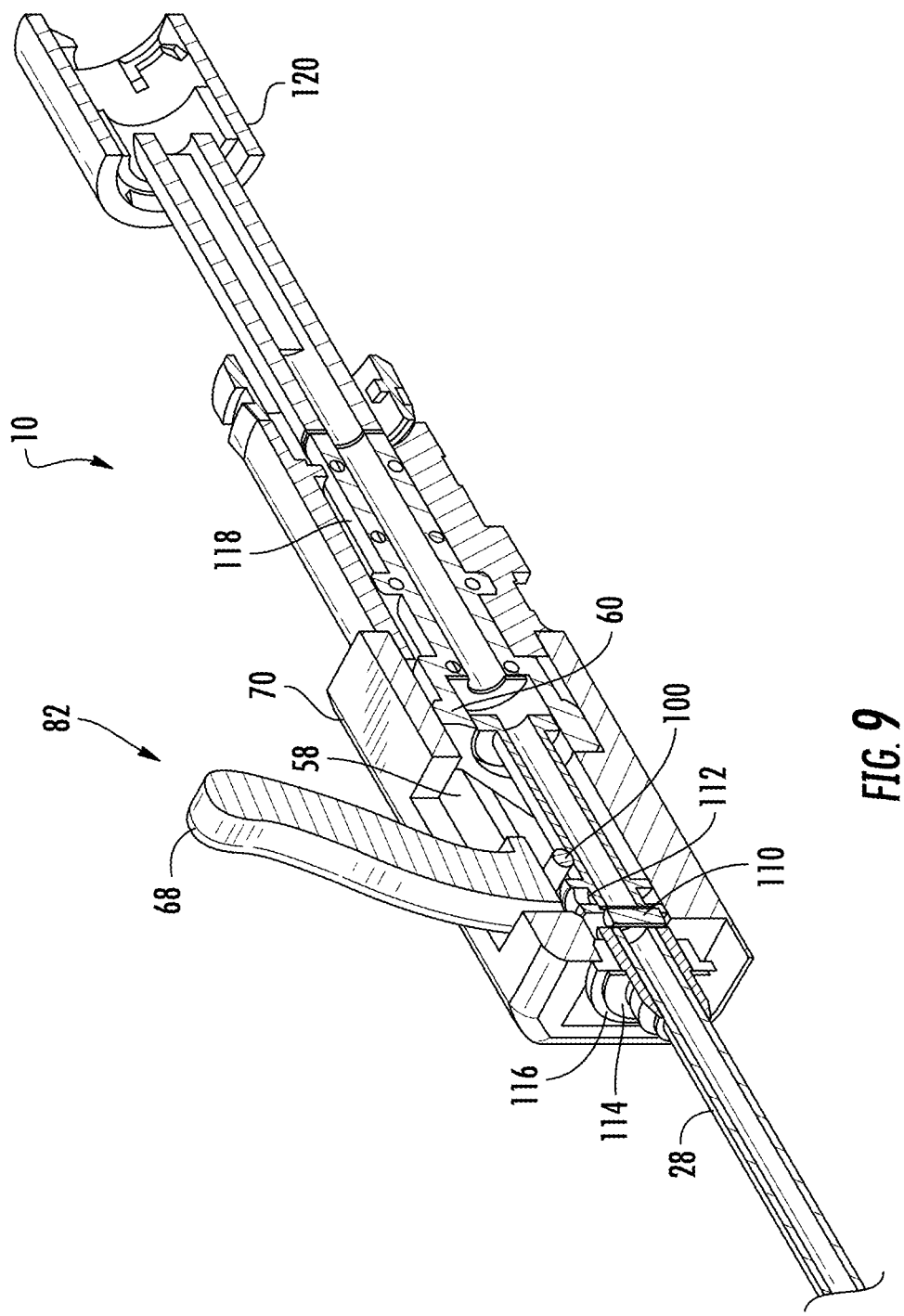
FIG. 9 is a cross-sectional, perspective view of the proximal end of the medical device taken at section line 9-9 in FIG. 8.
Figure 10:
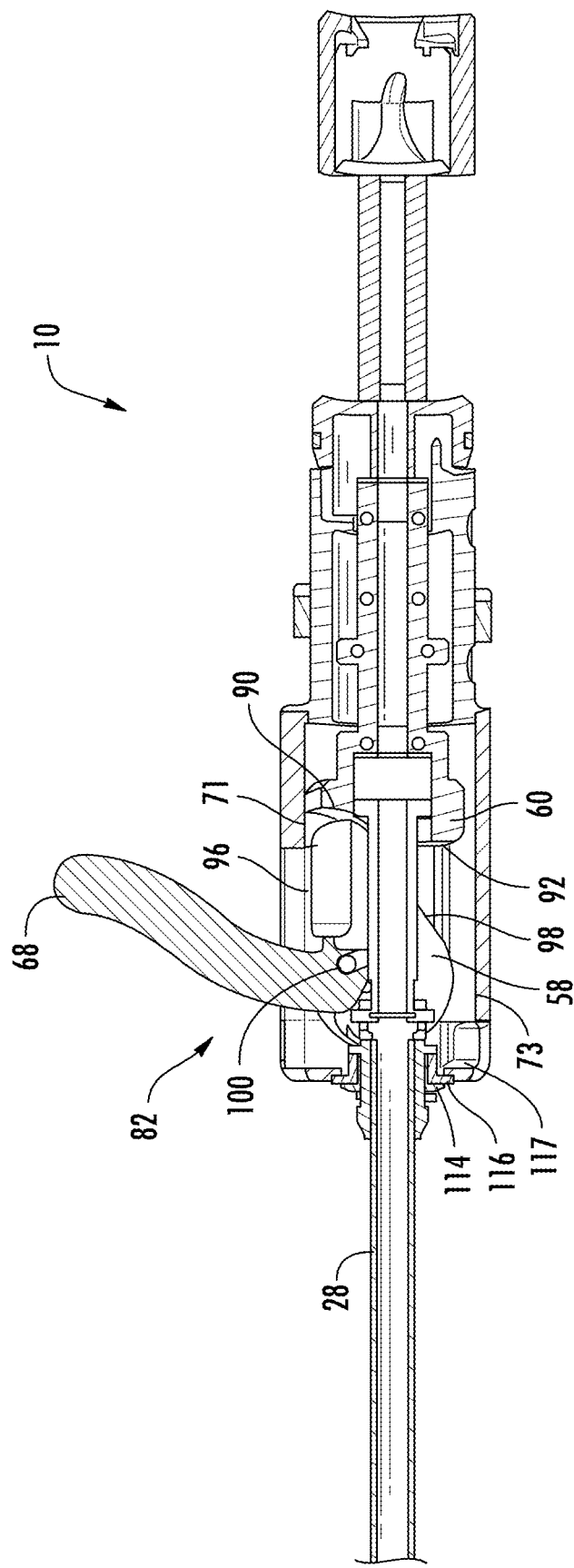
FIG. 10 is a cross-sectional side view of the proximal end of the medical device taken at section line 9-9 in FIG. 8.
Figure 11:
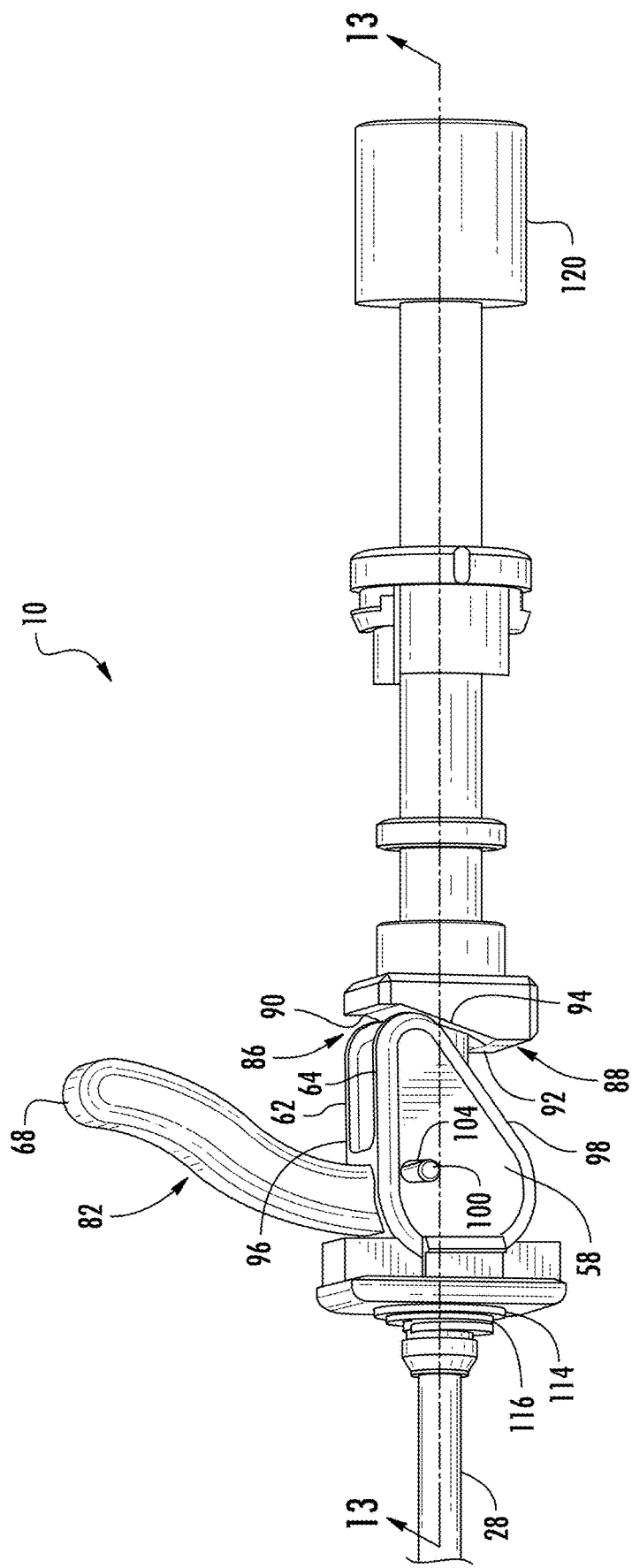
FIG. 11 is a side view of the proximal end of the medical device with the housing removed.
Figure 12:
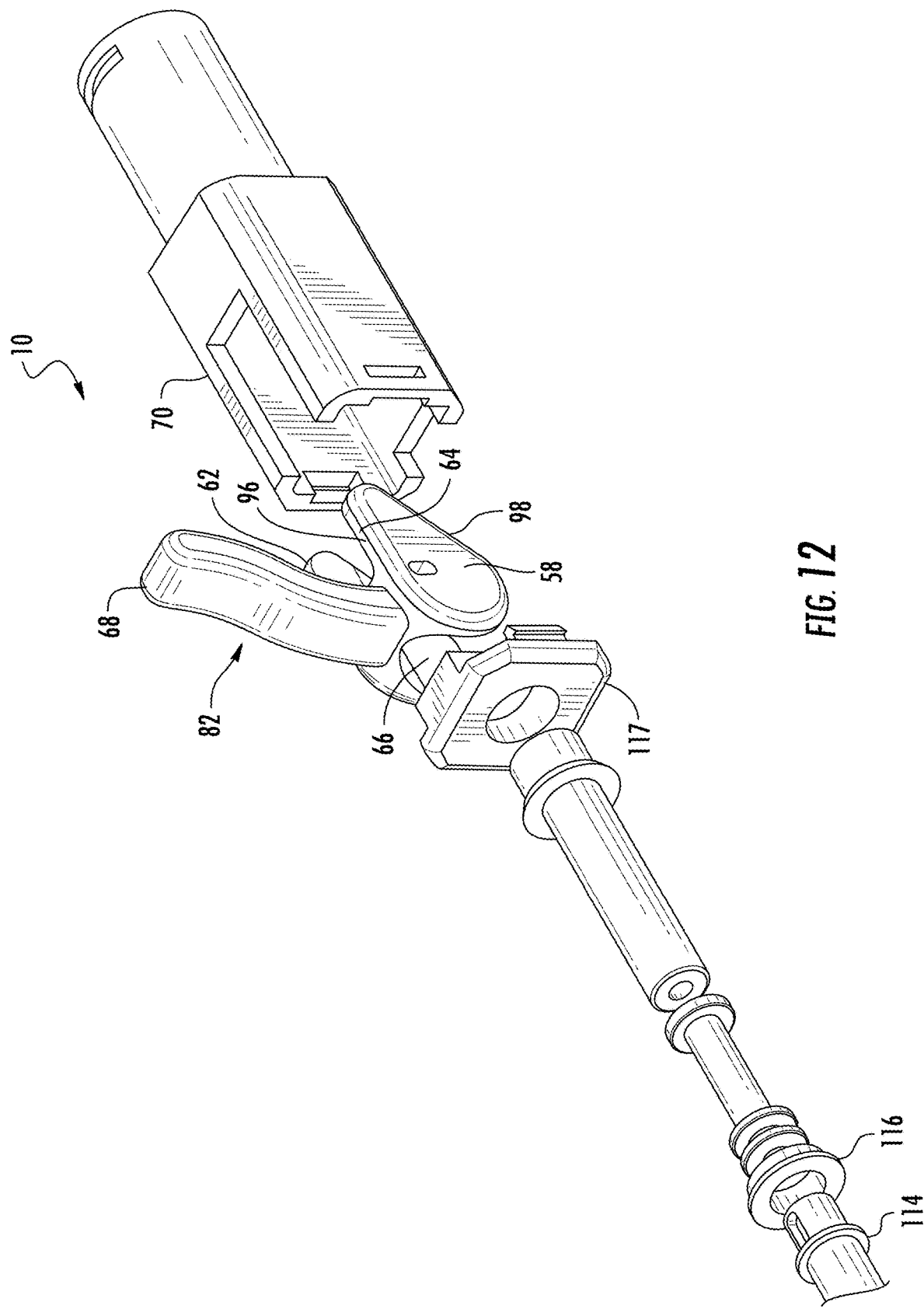
FIG. 12 is an exploded, perspective view of the proximal end of the medical device with the cam follower removed.
Figure 13:
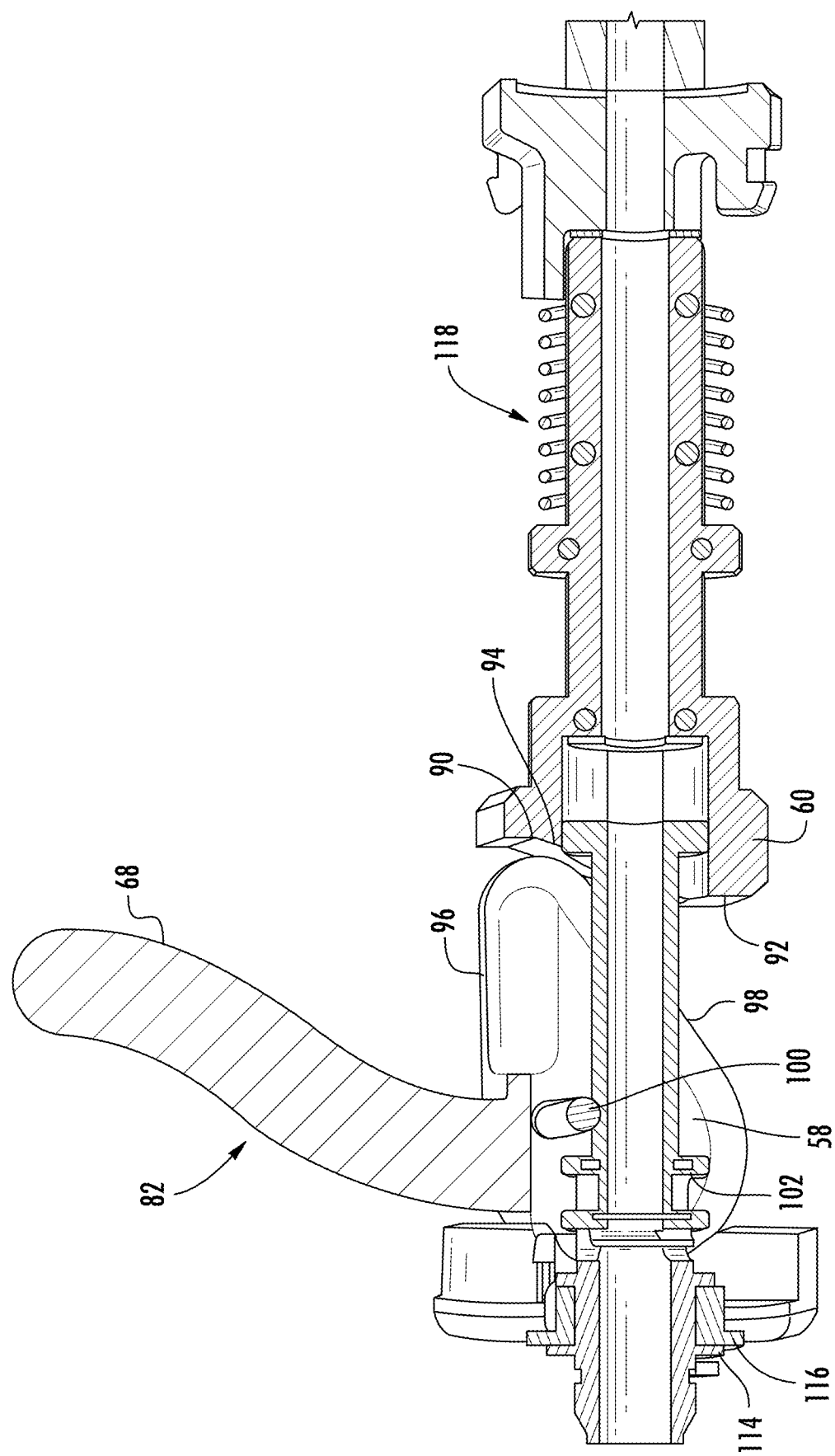
FIG. 13 is a cross-sectional side view of the proximal end of the medical device with the housing removed taken at section line 13-13 in FIG. 11.

In at least one embodiment, the inner and outer tubes 24, 28 may rotate together. The outer tube 28 may support the inner shaft 24. The inner and outer tubes 24, 28 may be coupled together in any appropriate manner that enables the inner shaft 24 or outer tube 28 to move relative to the other. In at least one embodiment, the inner shaft 24 may be coupled to the outer tube 28 via a pin 110 attached to the outer tube 28 and extending radially inward into a slot 112 positioned in the inner shaft 24. The slot 112 in the outer tube 28, as shown in FIG. 9, enables the inner shaft 24 to move axially relative to the outer tube 28.

The device 10 may include a flange 114 attached to the outer tube 28 to reduce friction between outer tube 28 and housing 70 to enable the outer tube 28 to rotate. In at least one embodiment, the device 10 may include a flange 114 attached to the outer tube 28 to reduce friction between outer tube 28 and a bushing 116 fitted within a cap 117 at a distal end of the housing 70 to enable the outer tube 28 to rotate. The flange 114 may support a bushing 116 attached to a cap 117, as shown in FIGS. 9-12, configured to be attached to a distal end of the housing 70. The bushing 116 enables the outer tube 28 to rotate without melting the cap 117.

Figure 2:
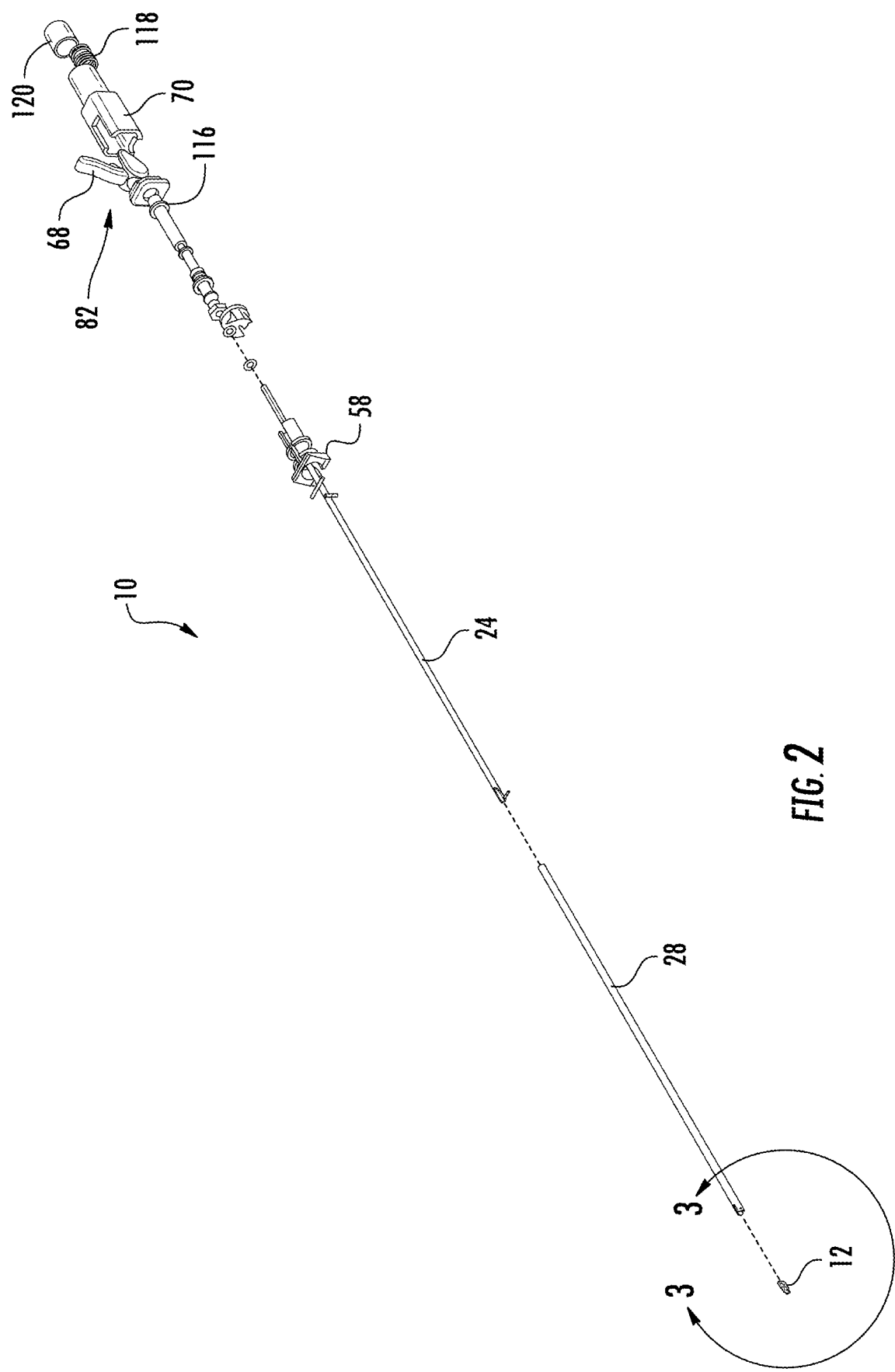
FIG. 2 is an exploded perspective view of the medical device of FIG. 1.
Figure 3:
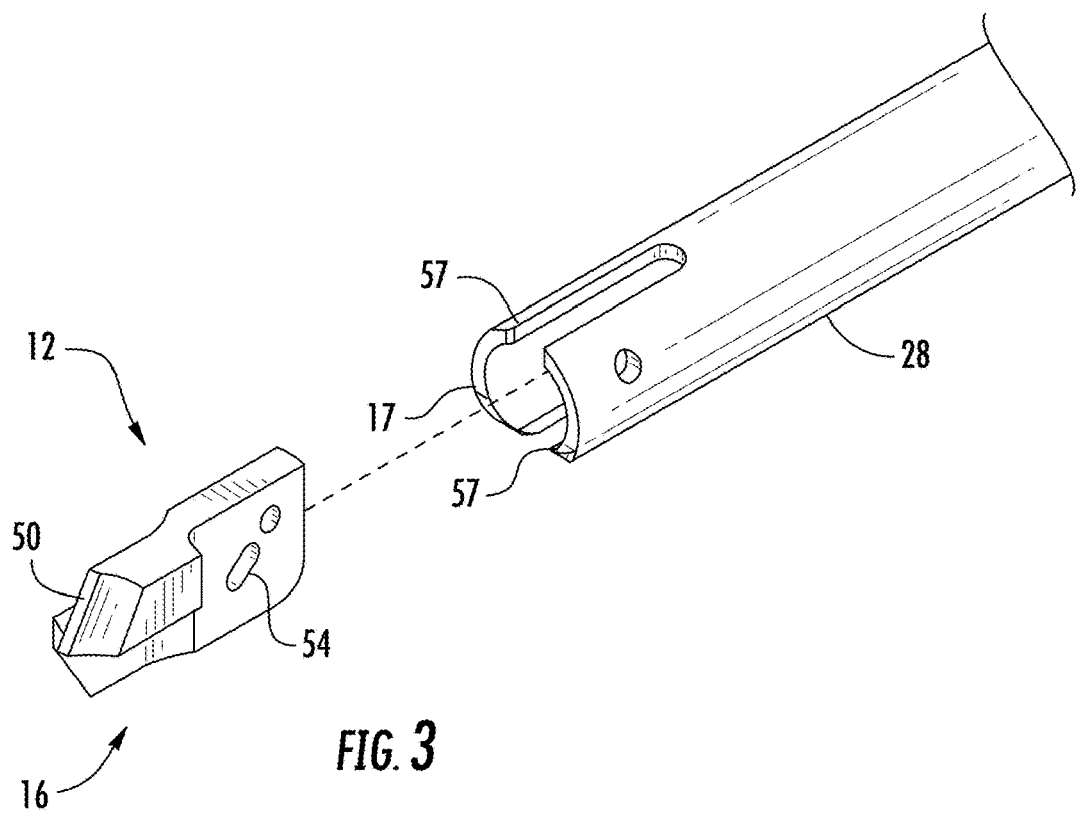
FIG. 3 is a perspective view detail of the distal end of the medical device taken at Detail 3-3 in FIG. 2.

The device 10 may also include a biasing mechanism 118, as shown in FIG. 2, configured to bias the cam follower 60 towards the cam 58 to keep the cam follower 60 in contact with the cam 58 and configured to bias the inner shaft 24 toward the distal end 14 of the elongated body 36. The biasing mechanism 118 may bias the cam follower 60 toward the distal end 14 and into contact with the cam 58. In at least one embodiment, the biasing mechanism 118 may be configured to be a compression spring.

The device 10 may also include a drive hub 120 positioned at the proximal end 38. The drive hub 120 may be configured to place the inner shaft 24 in mechanical communication with a handpiece to impart rotary motion to the inner shaft 24 and blade 12, and, in at least one embodiment, the outer tube 28, as controlled by controls on the handpiece of the device 10. The drive hub 120 may be detachable from the handpiece, thereby enabling other instruments to be attached to and driven by the same handpiece.

Figure 14:
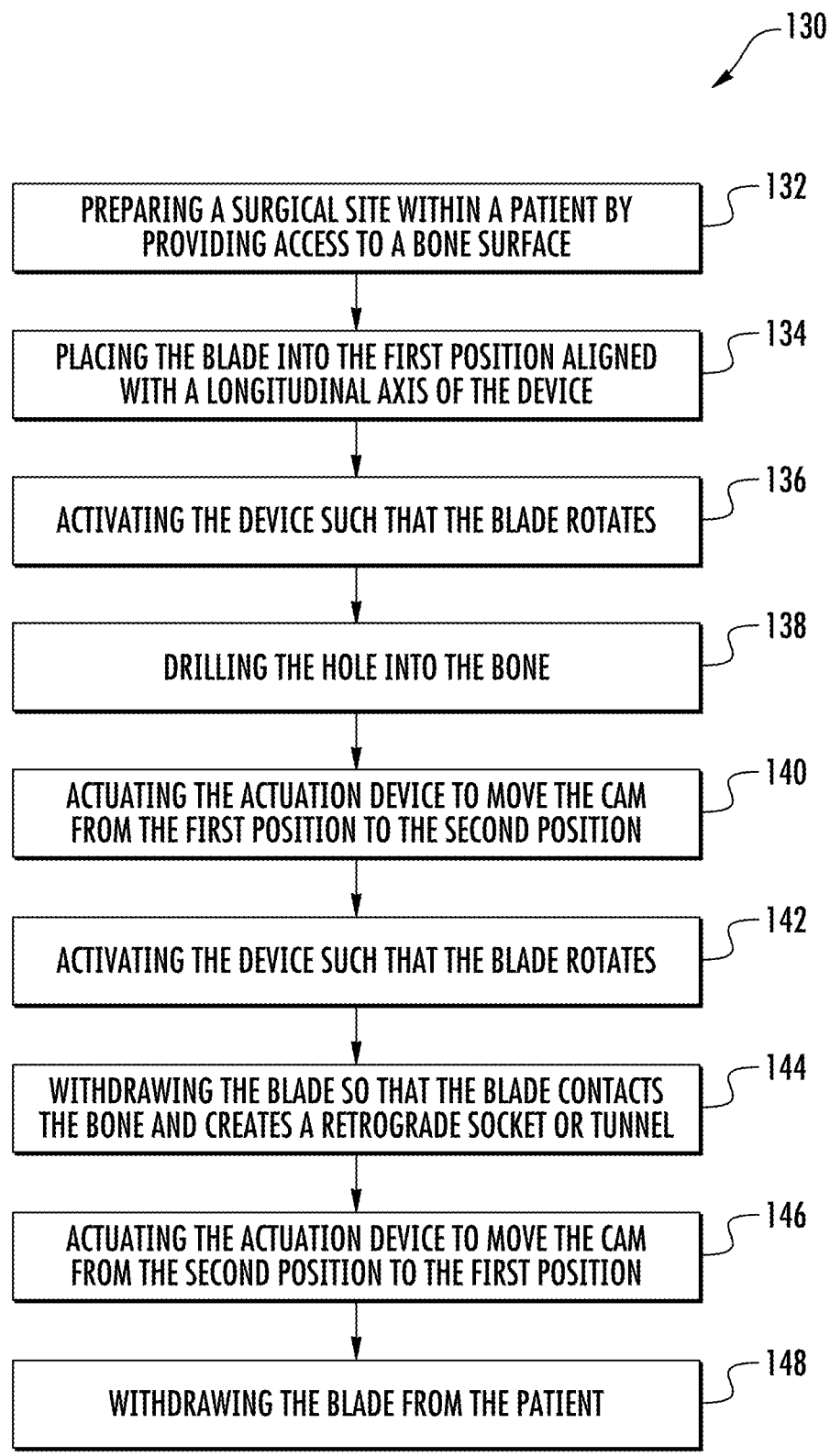
FIG. 14 is a flow chart of the method of using the medical device.
Figure 15:
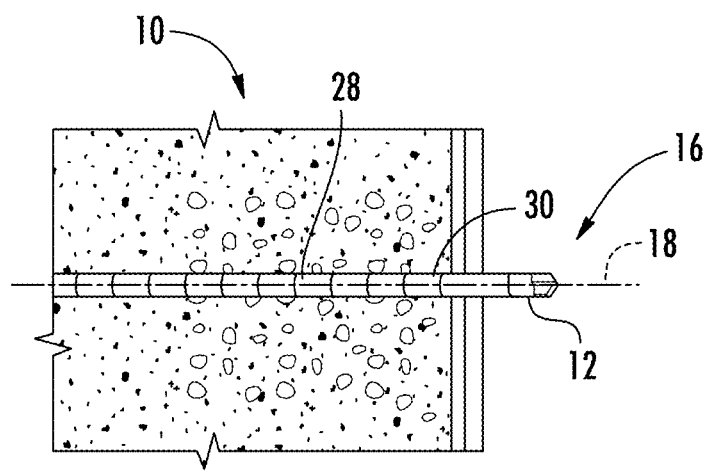
FIG. 15 is a cross-sectional side view of the outer tube and inner shaft being drilled through a bone of a patient with the blade positioned in the first position.
Figure 16:
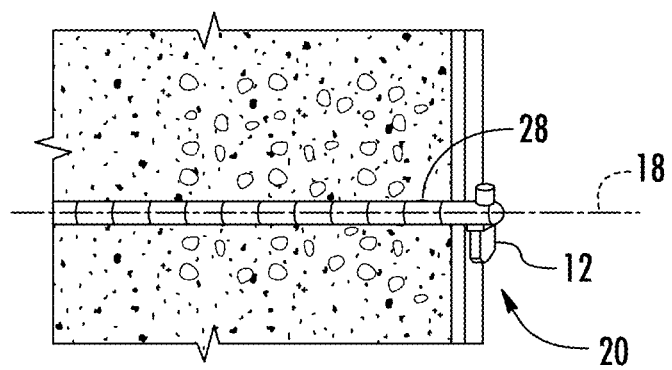
FIG. 16 is a cross-sectional side view of the outer tube and inner shaft being drilled through a bone of a patient with the blade positioned in the second flipped position.
Figure 17:
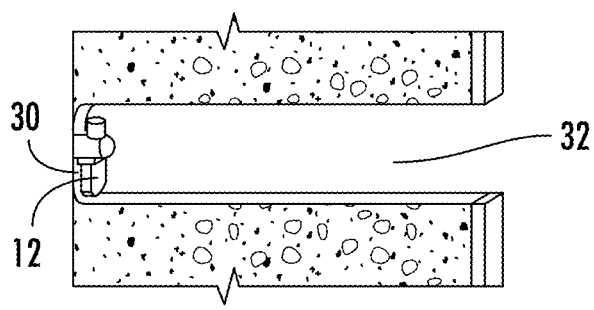
FIG. 17 is a cross-sectional side view of the outer tube and inner shaft with the blade positioned in the second flipped position and used to drill a retrograde socket.

As shown in FIG. 14, a method 130 of retrograde drilling of sockets for ACL reconstruction surgery using the device 10 may include preparing a surgical site within a patient by providing access to a bone surface at step 132. The method 130 may include at step 134 placing the blade 12 into the first position 16 aligned with a longitudinal axis 18 of the device 10. The method 130 may include at step 136 activating the device 10 such that the blade 12 rotates. The blade 12 may rotate with sufficient revolutions per minute (rpm) to drill into the bone. The method 130 may include at step 138 drilling the hole 30 into the bone in a patient. Once the blade 12 has completely passed through the bone, the method 130 may include at step 140 actuating the actuation device 68 to move the cam 58 from the first position 82 to the second position 84, which causes the blade 12 to be moved from the first position 16 aligned with a longitudinal axis 18 of the device 10 to the second position 20 nonparallel to the longitudinal axis 18 to create a retrograde socket 32 or tunnel. The method 130 may include at step 142 activating the device 10 such that the blade 12 rotates. The method 130 may include at step 144 may include withdrawing the blade 12 so that the blade 12 contacts the bone and creates a retrograde socket 32 or tunnel. The blade should be withdrawn less than a full length of the hole 30 in the bone. The method 130 may include at step 146 actuating the actuation device 68 to move the cam 58 from the second position 84 to the first position 82, which causes the blade 12 to be moved from the second position 20 nonparallel to the longitudinal axis 18 to the first position 16 aligned with a longitudinal axis 18 of the device 10. The method 130 may include at step 148 withdrawing the blade 12 from the patient.

In one embodiment, the step 140 for actuating the actuation device 68 may include actuating the device to move the blade 12 such that the blade 12 is positioned in a third position 21 between the first position 16, which may be at 0 degrees, and the second position 20, which may be at 90 degrees. In another embodiment, the step 140 for actuating the actuation device 68 may include actuating the device to move the blade 12 such that the blade 12 is positioned in a position between the first position 16, which may be at 0 degrees, and the third position 21, which may be at 45 degrees. In yet another embodiment, the step 140 for actuating the actuation device 68 may include actuating the device to move the blade 12 such that the blade 12 is positioned in a position between the second position 20, which may be at 90 degrees, and the third position 21, which may be at 45 degrees.

The method 130 may also include creating compound sockets, counterbores and countersinks within bone. The method 130 may include creating a hole as previously set forth. The blade 12, when not in contact with the bone, may be moved into a position in which the blade is closer to the 90 degree flipped position 20 than the 0 degree starting position 16. The blade 12 may then be moved into contact with the bone by partially withdrawing the inner shaft 24 and outer tube 28 from the hole. The blade 12 may create a socket when the inner shaft 24 and blade 12 are rotated together as the inner shaft 24 and outer tube 28 from the hole are partially withdrawn from the hole. In at least one embodiment, the outer tube 28 may rotate together with the inner shaft 24 and the blade 12. Once a socket having a desired length has been created, the blade 12 may be returned to the first position 16 to withdraw the blade 12 from the hole. This same procedure may be undertaken to create hole with varying degrees of counter sink at the bottom of the hole. The position of the blade 12 may be changed multiple times to create varying degrees of counter sink at the bottom of the hole.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A rotary cutting device comprising:
an elongated body having a distal end, a proximal end, and a longitudinal axis, the elongated body further comprising an outer tube and an inner shaft housed by the outer tube;
a blade at the distal end of the body, wherein the blade is configured to rotate from a first position generally aligned with the longitudinal axis to a second, flip position which is nonparallel with the longitudinal axis; and
a blade position control system connecting the blade to distal ends of both the outer tube and inner shaft, wherein the blade position control system comprises:
a connection system connecting the inner shaft to the blade that allows the blade to move from the first position generally aligned with the longitudinal axis to the second, flip position which is nonparallel with the longitudinal axis and a cutting arris of the blade is exposed toward the proximal end of the elongated body for retrograde drilling of a hole when the blade is locked in the second, flip position;
a cam in communication with a cam follower and in communication with the inner shaft for moving the blade into first and second positions;
a position retention system configured to retain the cam in a second position such that the inner shaft is retained in the second position, thereby retaining the cutting arris of the blade in position such that the cutting arris is exposed toward the proximal end of the elongated body for retrograde drilling of a hole while allowing the inner shaft and blade to rotate; and
wherein the position retention system is configured such that the cam follower includes a first position retainer configured to retain the cam in a first position, which also retains the blade in a position generally aligned with the longitudinal axis, and a second position retainer configured to retain the cam in a second position in which the cutting arris of the blade is positioned such that the cutting arris is exposed toward the proximal end of the elongated body while allowing the inner shaft and blade to rotate for retrograde drilling of a hole, wherein the first position retainer is formed from a flat surface on the cam generally orthogonal to the longitudinal axis of the elongated body, which also retains the blade in a position generally aligned with the longitudinal axis, and wherein the second position retainer is formed from a flat surface on the cam generally orthogonal to the longitudinal axis of the elongated body.

2. The rotary cutting device of claim 1, wherein the position retention system includes at least one pin extending from the cam.

3. The rotary cutting device of claim 2, wherein the position retention system includes at least one groove on the inner shaft for receiving the at least one pin extending from the cam such that the inner shaft is rotatable while the at least one pin resides in the at least one groove on the inner shaft, thereby preventing axial movement of the inner shaft.

4. The rotary cutting device of claim 3, wherein the position retention system includes at least one slot in the cam for receiving the at least one pin to account for potential misalignment between the pin, cam and at least one groove on the inner shaft.

5. The rotary cutting device of claim 1, wherein the cam is formed from a first head member and a second head member separated by a tube receiving chamber configured to receive the inner shaft extending therethrough.

6. The rotary cutting device of claim 1, wherein the engaging surface of the cam follower between the first and second position retainers is nonorthogonal relative to the longitudinal axis of the elongated body.

7. The rotary cutting device of claim 1, wherein the second position retainer is positioned closer to the distal end of the elongated body than the first position retainer.

8. The rotary cutting device of claim 1, further comprising a third position retainer positioned between the first and second retainers for retaining the cam in a third position in which the blade is positioned between the first and second positions.

9. The rotary cutting device of claim 1, further comprising a fourth position retainer positioned between the first and third retainers for retaining the cam in a fourth position which corresponds to a blade position between 10 degrees and 40 degrees.

10. The rotary cutting device of claim 1, further comprising a fifth position retainer positioned between the second and third retainers for retaining the cam in a fifth position between which corresponds to a blade position 50 degrees and 80 degrees.

11. The rotary cutting device of claim 1, further comprising a housing configured to retain the cam in position whereby the housing includes an inner side surface that houses the cam to prevent the cam from being inadvertently displaced and to limit rotation of the cam about only one axis.

12. The rotary cutting device of claim 1, further comprising a biasing mechanism configured to bias the cam follower towards the cam to keep the cam follower in contact with the cam and configured to bias the inner shaft toward the distal end of the elongated body.

13. The rotary cutting device of claim 1, further comprising a drive hub positioned at the proximal end, wherein the drive hub is configured to place the inner shaft in mechanical communication with a handpiece to impart rotary motion to the inner shaft and blade, as controlled by controls on the handpiece.

14. The rotary cutting device of claim 13, wherein the position retention system includes at least one slot in the cam for receiving the at least one pin to account for potential misalignment between the pin, cam and at least one groove on the inner shaft.

15. The rotary cutting device of claim 13, further comprising a housing configured to retain the cam in position whereby the housing includes an inner side surface that houses the cam to prevent the cam from being inadvertently displaced an to limit rotation of the cam about only one axis;
a biasing mechanism configured to bias the cam follower towards the cam to keep the cam follower in contact with the cam and configured to bias the inner shaft toward the distal end of the elongated body; and
a drive hub positioned at the proximal end, wherein the drive hub is configured to place the inner shaft in mechanical communication with a handpiece to impart rotary motion to the inner shaft and blade, as controlled by controls on the handpiece.

16. The rotary cutting device of claim 1, wherein the connection system connecting the inner shaft to the blade comprises a pin and a slot that allow conversion of linear movement of the inner shaft into rotational movement of the blade to rotate the blade to the second, flip position upon linear movement of the inner shaft in relation to the outer tube the pin sliding in the slot to permit rotation of the blade, and wherein the blade is articulated to a nonparallel position relative to the longitudinal axis of the elongated body when the blade is in the second, flip position, and wherein the second, flip position, the cutting arris of the blade is exposed toward the proximal end of the elongated body for retrograde drilling of a hole when the blade is locked in the second, flip position.

17. A rotary cutting device comprising:
   an elongated body having a distal end, a proximal end, and a longitudinal axis, the elongated body further comprising an outer tube and an inner shaft housed by the outer tube;
   a blade at the distal end of the body, wherein the blade is configured to rotate from a first position generally aligned with the longitudinal axis to a second, flip position which is nonparallel with the longitudinal axis; and
   a blade position control system connecting the blade to distal ends of both the outer tube and inner shaft, wherein the blade position control system comprises:
      a connection system connecting the inner shaft to the blade that allows the blade to move from the first position generally aligned with the longitudinal axis to the second, flip position which is nonparallel with the longitudinal axis and a cutting arris of the blade is exposed toward the proximal end of the elongated body for retrograde drilling of a hole when the blade is locked in the second, flip position;
      a cam in communication with a cam follower and in communication with the inner shaft for moving the blade into first and second positions, wherein the cam follower includes a first position retainer configured to retain the cam in a first position, which also retains the blade in a position generally aligned with the longitudinal axis, and a second position retainer configured to retain the cam in a second position in which the cutting arris of the blade is positioned such that the cutting arris is exposed toward the proximal end of the elongated body for retrograde drilling of a hole while allowing the inner shaft and blade to rotate; and
      a position retention system configured to retain the cam in a second position such that the inner shaft is retained in the second position, thereby retaining the cutting arris of the blade in position such that the cutting arris is exposed toward the proximal end of the elongated body for retrograde drilling of a hole while allowing the inner shaft and blade to rotate;
   wherein the position retention system includes at least one pin extending from the cam and wherein the position retention system includes at least one groove on the inner shaft for receiving the at least one pin extending from the cam such that the inner shaft is rotatable while the at least one pin resides in the at least one groove on the inner shaft, thereby preventing axial movement of the inner shaft; and
   wherein the position retention system is configured such that the cam follower includes a first position retainer configured to retain the cam in a first position, which also retains the blade in a position generally aligned with the longitudinal axis, and a second position retainer configured to retain the cam in a second position in which the cutting arris of the blade is positioned such that the cutting arris is exposed toward the proximal end of the elongated body while allowing the inner shaft and blade to rotate for retrograde drilling of a hole, wherein the first position retainer is formed from a flat surface on the cam generally orthogonal to the longitudinal axis of the elongated body, which also retains the blade in a position generally aligned with the longitudinal axis, and wherein the second position retainer is formed from a flat surface on the cam generally orthogonal to the longitudinal axis of the elongated body.

* * * * *